(12) United States Patent
Hartwell et al.

(10) Patent No.: US 11,596,552 B2
(45) Date of Patent: *Mar. 7, 2023

(54) WOUND DRESSING AND METHOD OF TREATMENT

(71) Applicant: Smith & Nephew PLC, Watford (GB)

(72) Inventors: Edward Yerbury Hartwell, Hull (GB); Varuni Rachindra Brownhill, Swanland (GB); John Gowans, Hessle (GB)

(73) Assignee: Smith & Nephew PLC, Watford (GB)

( * ) Notice: Subject to any disclaimer, the term of this patent is extended or adjusted under 35 U.S.C. 154(b) by 481 days.

This patent is subject to a terminal disclaimer.

(21) Appl. No.: 16/841,516

(22) Filed: Apr. 6, 2020

(65) Prior Publication Data

US 2020/0297541 A1 Sep. 24, 2020

Related U.S. Application Data

(63) Continuation of application No. 15/319,743, filed as application No. PCT/EP2015/063373 on Jun. 15, 2015, now Pat. No. 10,610,414.

(Continued)

(51) Int. Cl.
*A61M 1/00* (2006.01)
*A61F 13/00* (2006.01)
(Continued)

(52) U.S. Cl.
CPC .. *A61F 13/00029* (2013.01); *A61F 13/00008* (2013.01); *A61F 13/00068* (2013.01);
(Continued)

(58) Field of Classification Search
CPC ......... A61M 1/00; A61M 27/00; A61F 13/00; A61F 13/02; A61F 13/00029;
(Continued)

(56) References Cited

U.S. PATENT DOCUMENTS 3,972,328 A 8/1976 Chen
4,029,598 A 6/1977 Neisius et al.
(Continued)

FOREIGN PATENT DOCUMENTS

CN 101744688 6/2010
CN 102038575 5/2011
(Continued)

OTHER PUBLICATIONS

U.S. Appl. No. 61/828,604, filed May 29, 2013, Collinson et al.
(Continued)

*Primary Examiner* — Michele M Kidwell
*Assistant Examiner* — Ilya Y Treyger
(74) *Attorney, Agent, or Firm* — Knobbe, Martens, Olson & Bear, LLP

(57) ABSTRACT

Embodiments disclosed herein are directed to negative pressure treatment systems and wound dressing systems, apparatuses, and methods that may be used for the treatment of wounds. In particular, some embodiments are directed to improved wound dressings comprising a number of viewing portals that facilitate observation of wound tissue or healthy skin underlying the wound dressing. Some embodiments of the viewing portals are provided by forming through holes in internal dressing layers including absorbent material and transmission material, optionally by providing a plug material within the through holes, and by providing translucent or transparent cover layer and tissue contact layer materials.

17 Claims, 26 Drawing Sheets

Related U.S. Application Data

(60) Provisional application No. 62/013,989, filed on Jun. 18, 2014, provisional application No. 62/085,774, filed on Dec. 1, 2014.

(51) Int. Cl.
*A61F 13/02* (2006.01)
*A61M 27/00* (2006.01)
*A61K 9/22* (2006.01)

(52) U.S. Cl.
CPC ........ *A61F 13/022* (2013.01); *A61F 13/0216* (2013.01); *A61F 13/0233* (2013.01); *A61F 2013/00182* (2013.01)

(58) Field of Classification Search
CPC .......... A61F 13/00008; A61F 13/00068; A61F 13/0216; A61F 13/022; A61F 13/0233; A61F 2013/00182; A61K 9/22
See application file for complete search history.

(56) References Cited

U.S. PATENT DOCUMENTS

| | | |
|---|---|---|
| 4,728,499 A | 3/1988 | Fehder |
| 4,798,603 A | 1/1989 | Meyer et al. |
| 4,813,942 A | 3/1989 | Alvarez |
| 4,834,735 A | 5/1989 | Alemany et al. |
| 4,846,164 A | 7/1989 | Martz |
| 4,968,181 A | 11/1990 | Goldman |
| 4,973,325 A | 11/1990 | Sherrod et al. |
| 4,988,344 A | 1/1991 | Reising et al. |
| 4,988,345 A | 1/1991 | Reising |
| 5,021,050 A | 6/1991 | Iskra |
| 5,037,409 A | 8/1991 | Chen et al. |
| 5,056,510 A | 10/1991 | Gilman |
| 5,065,600 A | 11/1991 | Byles |
| 5,124,197 A | 6/1992 | Bernardin et al. |
| 5,149,334 A | 9/1992 | Lahrman et al. |
| 5,149,469 A | 9/1992 | Komatsuzaki et al. |
| 5,151,091 A | 9/1992 | Glaug et al. |
| 5,171,391 A | 12/1992 | Chmielewski et al. |
| 5,175,046 A | 12/1992 | Nguyen |
| 5,181,905 A | 1/1993 | Flam |
| 5,217,445 A | 6/1993 | Young et al. |
| 5,236,427 A | 8/1993 | Hamajima et al. |
| 5,238,732 A | 8/1993 | Krishnan |
| 5,242,435 A | 9/1993 | Murji et al. |
| 5,257,982 A | 11/1993 | Cohen et al. |
| 5,271,987 A | 12/1993 | Iskra |
| 5,281,208 A | 1/1994 | Thompson et al. |
| 5,294,478 A | 3/1994 | Wanek et al. |
| 5,296,290 A | 3/1994 | Brassington |
| 5,314,743 A | 5/1994 | Meirowitz et al. |
| 5,318,554 A | 6/1994 | Young et al. |
| 5,330,456 A | 7/1994 | Robinson |
| 5,342,336 A | 8/1994 | Meirowitz et al. |
| 5,348,547 A | 9/1994 | Payne et al. |
| 5,356,405 A | 10/1994 | Thompson et al. |
| 5,360,420 A | 11/1994 | Cook et al. |
| 5,364,382 A | 11/1994 | Latimer et al. |
| 5,366,451 A | 11/1994 | Levesque |
| 5,368,909 A | 11/1994 | Langdon et al. |
| 5,368,926 A | 11/1994 | Thompson et al. |
| 5,374,260 A | 12/1994 | Lemay et al. |
| 5,382,245 A | 1/1995 | Thompson et al. |
| 5,387,208 A | 2/1995 | Ashton et al. |
| 5,397,316 A | 3/1995 | LaVon et al. |
| 5,401,267 A | 3/1995 | Couture-Dorschner et al. |
| 5,425,725 A | 6/1995 | Tanzer et al. |
| 5,431,643 A | 7/1995 | Ouellette et al. |
| 5,454,800 A | 10/1995 | Hirt et al. |
| 5,465,735 A | 11/1995 | Patel |
| 5,470,326 A | 11/1995 | Dabi et al. |
| H1511 H | 12/1995 | Chappell et al. |
| 5,486,167 A | 1/1996 | Dragoo et al. |
| 5,500,270 A | 3/1996 | Langdon et al. |
| 5,505,719 A | 4/1996 | Cohen et al. |
| 5,509,914 A | 4/1996 | Osborn, III |
| 5,514,120 A | 5/1996 | Johnston et al. |
| 5,525,407 A | 6/1996 | Yang |
| 5,536,264 A | 7/1996 | Hsueh et al. |
| 5,538,500 A | 7/1996 | Peterson |
| H1585 H | 8/1996 | Ahr |
| 5,545,155 A | 8/1996 | Hseih et al. |
| 5,549,584 A | 8/1996 | Gross |
| 5,549,589 A | 8/1996 | Horney et al. |
| 5,562,107 A | 10/1996 | Lavender et al. |
| 5,562,646 A | 10/1996 | Goldman et al. |
| 5,562,650 A | 10/1996 | Everett et al. |
| 5,591,148 A | 1/1997 | McFall et al. |
| 5,591,149 A | 1/1997 | Cree et al. |
| 5,603,707 A | 2/1997 | Trombetta et al. |
| 5,609,588 A | 3/1997 | DiPalma et al. |
| 5,613,960 A | 3/1997 | Mizutani |
| 5,614,283 A | 3/1997 | Pontis et al. |
| 5,614,295 A | 3/1997 | Quincy, III et al. |
| 5,628,736 A | 5/1997 | Thompson |
| 5,632,731 A | 5/1997 | Patel |
| H1657 H | 6/1997 | Hammons et al. |
| 5,634,915 A | 6/1997 | Osterdahl |
| 5,643,238 A | 7/1997 | Baker |
| 5,648,142 A | 7/1997 | Phillips |
| 5,649,915 A | 7/1997 | Chauvette et al. |
| 5,649,916 A | 7/1997 | DiPalma et al. |
| 5,665,082 A | 9/1997 | Boulanger |
| 5,669,895 A | 9/1997 | Murakami et al. |
| 5,675,079 A | 10/1997 | Gilman et al. |
| 5,700,254 A | 12/1997 | McDowall et al. |
| 5,704,905 A | 1/1998 | Jensen et al. |
| 5,707,499 A | 1/1998 | Joshi et al. |
| 5,716,703 A | 2/1998 | Payne |
| 5,728,084 A | 3/1998 | Palumbo et al. |
| 5,728,085 A | 3/1998 | Widlund et al. |
| 5,733,273 A | 3/1998 | Ahr |
| 5,752,945 A | 5/1998 | Mosley et al. |
| 5,759,570 A | 6/1998 | Arnold |
| 5,762,641 A | 6/1998 | Bewick-Sonntag et al. |
| 5,788,684 A | 8/1998 | Abuto et al. |
| 5,801,107 A | 9/1998 | Everhart et al. |
| 5,810,798 A | 9/1998 | Finch et al. |
| 5,817,081 A | 10/1998 | LaVon et al. |
| 5,827,213 A | 10/1998 | Jensen |
| 5,827,254 A | 10/1998 | Trombetta et al. |
| 5,830,202 A | 11/1998 | Bogdanski et al. |
| 5,837,627 A | 11/1998 | Halabisky et al. |
| 5,843,025 A | 12/1998 | Shaari |
| 5,843,064 A | 12/1998 | Koczab |
| 5,852,126 A | 12/1998 | Barnard et al. |
| 5,855,572 A | 1/1999 | Schmidt |
| 5,865,822 A | 2/1999 | Hamajima et al. |
| 5,865,824 A | 2/1999 | Chen et al. |
| 5,873,867 A | 2/1999 | Coles et al. |
| 5,877,097 A | 3/1999 | West et al. |
| 5,891,120 A | 4/1999 | Chmielewski |
| 5,895,379 A | 4/1999 | Litchholt et al. |
| 5,897,541 A | 4/1999 | Uitenbrock et al. |
| 5,916,507 A | 6/1999 | Dabi et al. |
| 5,925,026 A | 7/1999 | Arteman et al. |
| 5,931,823 A | 8/1999 | Stokes et al. |
| 5,938,995 A | 8/1999 | Koltisko, Jr. et al. |
| 5,941,863 A | 8/1999 | Guidotti et al. |
| 5,947,945 A | 9/1999 | Cree et al. |
| 5,951,535 A | 9/1999 | Fujiwara et al. |
| 5,961,506 A | 10/1999 | Guidotti et al. |
| 5,968,027 A | 10/1999 | Cole et al. |
| 5,989,478 A | 11/1999 | Ouellette et al. |
| 6,022,610 A | 2/2000 | Phan et al. |
| 6,037,518 A | 3/2000 | Guidotti et al. |
| 6,060,638 A | 5/2000 | Paul et al. |
| 6,068,620 A | 5/2000 | Chmielewski |
| 6,071,267 A | 6/2000 | Zamierowski |
| 6,077,526 A | 6/2000 | Scully et al. |
| 6,096,015 A | 8/2000 | Yeo et al. |

(56) References Cited

U.S. PATENT DOCUMENTS

| | | |
|---|---|---|
| 6,103,953 A | 8/2000 | Cree et al. |
| 6,103,954 A | 8/2000 | Grondin et al. |
| 6,107,539 A | 8/2000 | Palumbo et al. |
| 6,117,523 A | 9/2000 | Sugahara |
| 6,127,595 A | 10/2000 | Makoui et al. |
| 6,168,849 B1 | 1/2001 | Braverman et al. |
| 6,191,340 B1 | 2/2001 | Carlucci et al. |
| 6,206,865 B1 | 3/2001 | Chen et al. |
| 6,235,966 B1 | 5/2001 | Magnusson et al. |
| 6,264,776 B1 | 7/2001 | DiPalma |
| 6,294,710 B1 | 9/2001 | Schmidt et al. |
| 6,297,423 B1 | 10/2001 | Schoenfeldt et al. |
| 6,344,036 B1 | 2/2002 | Ivansson |
| 6,362,390 B1 | 3/2002 | Carlucci et al. |
| 6,369,292 B1 | 4/2002 | Strack et al. |
| 6,372,952 B1 | 4/2002 | Lash et al. |
| 6,403,857 B1 | 6/2002 | Gross et al. |
| 6,461,339 B1 | 10/2002 | Sugahara |
| 6,497,689 B1 | 12/2002 | Schmidt et al. |
| 6,506,175 B1 | 1/2003 | Goldstein |
| 6,506,960 B1 | 1/2003 | Young et al. |
| 6,521,813 B1 | 2/2003 | Chihani |
| 6,534,149 B1 | 3/2003 | Daley et al. |
| 6,545,194 B1 | 4/2003 | Schmidt et al. |
| 6,551,295 B1 | 4/2003 | Schmidt et al. |
| 6,552,244 B1 | 4/2003 | Jacques et al. |
| 6,570,057 B1 | 5/2003 | Schmidt et al. |
| 6,570,058 B1 | 5/2003 | Fuchs et al. |
| 6,573,424 B1 | 6/2003 | Raidel et al. |
| 6,586,653 B2 | 7/2003 | Graeme, III et al. |
| 6,610,898 B1 | 8/2003 | Magnusson et al. |
| 6,610,903 B1 | 8/2003 | Latimer et al. |
| 6,613,028 B1 | 9/2003 | Daley et al. |
| 6,613,953 B1 | 9/2003 | Altura |
| 6,613,955 B1 | 9/2003 | Lindsay et al. |
| 6,626,891 B2 | 9/2003 | Ohmstede |
| 6,630,611 B1 | 10/2003 | Malowaniec |
| 6,664,439 B1 | 12/2003 | Arndt et al. |
| 6,683,229 B1 | 1/2004 | Ehrnsperger et al. |
| 6,685,681 B2 | 2/2004 | Lockwood et al. |
| 6,719,742 B1 | 4/2004 | McCormack et al. |
| 6,727,403 B1 | 4/2004 | Ehrnsperger et al. |
| 6,752,794 B2 | 6/2004 | Lockwood et al. |
| 6,762,337 B2 | 7/2004 | Boukanov et al. |
| 6,764,459 B1 | 7/2004 | Donaldson |
| 6,783,837 B1 | 8/2004 | Creagan et al. |
| 6,835,192 B1 | 12/2004 | Guidotti et al. |
| 6,838,589 B2 | 1/2005 | Liedtke et al. |
| 6,936,037 B2 | 8/2005 | Bubb et al. |
| 6,951,553 B2 | 10/2005 | Bubb et al. |
| 6,979,324 B2 | 12/2005 | Bybordi et al. |
| 7,004,915 B2 | 2/2006 | Boynton et al. |
| 7,049,478 B1 | 5/2006 | Smith et al. |
| 7,070,584 B2 | 7/2006 | Johnson et al. |
| 7,108,683 B2 | 9/2006 | Zamierowski |
| 7,112,712 B1 | 9/2006 | Ancell |
| 7,122,023 B1 | 10/2006 | Hinoki |
| 7,216,651 B2 | 5/2007 | Argenta et al. |
| 7,361,184 B2 | 4/2008 | Joshi |
| 7,381,859 B2 | 6/2008 | Hunt et al. |
| 7,429,689 B2 | 9/2008 | Chen et al. |
| 7,511,187 B2 | 3/2009 | Kelly |
| 7,569,742 B2 | 8/2009 | Haggstrom et al. |
| 7,605,298 B2 | 10/2009 | Bechert et al. |
| 7,612,248 B2 | 11/2009 | Burton et al. |
| 7,615,036 B2 | 11/2009 | Joshi et al. |
| 7,622,629 B2 | 11/2009 | Aail |
| 7,625,362 B2 | 12/2009 | Boehringer et al. |
| 7,699,823 B2 | 4/2010 | Haggstrom et al. |
| 7,700,819 B2 | 4/2010 | Ambrosio et al. |
| 7,708,724 B2 | 5/2010 | Weston |
| 7,718,249 B2 | 5/2010 | Russell et al. |
| 7,722,582 B2 | 5/2010 | Lina et al. |
| 7,749,531 B2 | 7/2010 | Booher |
| 7,759,537 B2 | 7/2010 | Bishop et al. |
| 7,759,539 B2 | 7/2010 | Shaw et al. |
| 7,775,998 B2 | 8/2010 | Riesinger |
| 7,779,625 B2 | 8/2010 | Joshi et al. |
| 7,811,269 B2 | 10/2010 | Boynton et al. |
| 7,838,717 B2 | 11/2010 | Haggstrom et al. |
| 7,838,723 B1 | 11/2010 | Schmidt et al. |
| 7,846,141 B2 | 12/2010 | Weston |
| 7,910,791 B2 | 3/2011 | Coffey |
| 7,922,703 B2 | 4/2011 | Riesinger |
| 7,959,624 B2 | 6/2011 | Riesinger |
| 7,964,766 B2 | 6/2011 | Blott et al. |
| 7,976,519 B2 | 7/2011 | Bubb et al. |
| 7,982,087 B2 | 7/2011 | Greener et al. |
| 8,021,347 B2 | 9/2011 | Vitaris et al. |
| 8,034,037 B2 | 10/2011 | Adams et al. |
| 8,062,272 B2 | 11/2011 | Weston |
| 8,062,331 B2 | 11/2011 | Zamierowski |
| 8,080,702 B2 | 12/2011 | Blott et al. |
| 8,092,436 B2 | 1/2012 | Christensen |
| 8,118,794 B2 | 2/2012 | Weston et al. |
| 8,147,468 B2 | 4/2012 | Barta et al. |
| 8,152,785 B2 | 4/2012 | Vitaris |
| 8,158,844 B2 | 4/2012 | McNeil |
| 8,162,907 B2 | 4/2012 | Heagle |
| 8,188,331 B2 | 5/2012 | Barta et al. |
| 8,207,392 B2 | 6/2012 | Haggstrom et al. |
| 8,212,101 B2 | 7/2012 | Propp |
| 8,235,972 B2 | 8/2012 | Adahan |
| 8,241,261 B2 | 8/2012 | Randolph et al. |
| 8,252,971 B2 | 8/2012 | Aali et al. |
| 8,282,611 B2 | 10/2012 | Weston |
| 8,298,200 B2 | 10/2012 | Vess et al. |
| 8,303,552 B2 | 11/2012 | Weston |
| 8,314,283 B2 | 11/2012 | Kingsford et al. |
| 8,372,049 B2 | 2/2013 | Jaeb et al. |
| 8,372,050 B2 | 2/2013 | Jaeb et al. |
| 8,399,730 B2 | 3/2013 | Kazala, Jr. et al. |
| 8,404,921 B2 | 3/2013 | Lee et al. |
| 8,425,478 B2 | 4/2013 | Olson |
| 8,444,612 B2 | 5/2013 | Patel et al. |
| 8,460,255 B2 | 6/2013 | Joshi et al. |
| 8,535,296 B2 | 9/2013 | Blott et al. |
| 8,540,688 B2 | 9/2013 | Eckstein et al. |
| 8,545,466 B2 | 10/2013 | Andresen et al. |
| 8,568,386 B2 | 10/2013 | Malhi |
| 8,628,505 B2 | 1/2014 | Weston |
| 8,641,691 B2 | 2/2014 | Fink |
| 8,663,198 B2 | 3/2014 | Buan et al. |
| 8,680,360 B2 | 3/2014 | Greener et al. |
| 8,715,256 B2 | 5/2014 | Greener |
| 8,764,732 B2 | 7/2014 | Hartwell |
| 8,771,244 B2 | 7/2014 | Eckstein et al. |
| 8,791,316 B2 | 7/2014 | Greener |
| 8,795,243 B2 | 8/2014 | Weston |
| 8,795,247 B2 | 8/2014 | Bennett et al. |
| 8,795,800 B2 | 8/2014 | Evans |
| 8,801,685 B2 | 8/2014 | Armstrong et al. |
| 8,808,274 B2 | 8/2014 | Hartwell |
| 8,814,842 B2 | 8/2014 | Coulthard et al. |
| 8,829,263 B2 | 9/2014 | Haggstrom et al. |
| 8,834,451 B2 | 9/2014 | Blott et al. |
| 8,834,452 B2 | 9/2014 | Hudspeth et al. |
| 8,956,336 B2 | 2/2015 | Haggstrom et al. |
| 9,061,095 B2 | 6/2015 | Adie et al. |
| 9,067,003 B2 | 6/2015 | Buan et al. |
| 9,127,665 B2 | 9/2015 | Locke et al. |
| 9,168,330 B2 | 10/2015 | Joshi et al. |
| 9,199,012 B2 | 12/2015 | Vitaris et al. |
| 9,220,822 B2 | 12/2015 | Hartwell et al. |
| 9,283,118 B2 | 3/2016 | Locke et al. |
| 9,302,033 B2 | 4/2016 | Riesinger |
| 9,327,065 B2 | 5/2016 | Alberti et al. |
| 9,375,353 B2 | 6/2016 | Vitaris et al. |
| 9,375,521 B2 | 6/2016 | Hudspeth et al. |
| 9,381,283 B2 | 7/2016 | Adams et al. |
| 9,427,505 B2 | 8/2016 | Askem et al. |
| 9,446,178 B2 | 9/2016 | Blott et al. |
| 9,452,248 B2 | 9/2016 | Blott et al. |
| 9,474,653 B2 | 10/2016 | Luckemeyer et al. |

(56) References Cited

U.S. PATENT DOCUMENTS

| | | |
|---|---|---|
| 9,669,138 B2 | 6/2017 | Joshi et al. |
| 9,682,179 B2 | 6/2017 | May |
| 9,795,725 B2 | 10/2017 | Joshi et al. |
| 9,808,561 B2 | 11/2017 | Adie et al. |
| 9,844,473 B2 | 12/2017 | Blott et al. |
| 9,877,872 B2 | 1/2018 | Mumby et al. |
| 9,962,474 B2 | 5/2018 | Greener |
| 10,016,309 B2 | 7/2018 | Hartwell |
| 10,046,096 B2 | 8/2018 | Askem et al. |
| 10,130,519 B2 | 11/2018 | Mumby et al. |
| 10,201,644 B2 | 2/2019 | Haggstrom et al. |
| 10,610,414 B2 | 4/2020 | Hartwell et al. |
| 2001/0000795 A1 | 5/2001 | Bolian, II et al. |
| 2001/0016985 A1 | 8/2001 | Insley et al. |
| 2001/0018308 A1 | 8/2001 | Quick et al. |
| 2001/0027302 A1 | 10/2001 | Glaug et al. |
| 2001/0027305 A1 | 10/2001 | Raidel et al. |
| 2001/0044610 A1 | 11/2001 | Kim et al. |
| 2001/0053904 A1 | 12/2001 | Abuto |
| 2002/0007167 A1 | 1/2002 | Dan et al. |
| 2002/0007169 A1 | 1/2002 | Graef et al. |
| 2002/0019614 A1 | 2/2002 | Woon et al. |
| 2002/0026166 A1 | 2/2002 | Graef et al. |
| 2002/0034914 A1 | 3/2002 | De Leon et al. |
| 2002/0035352 A1 | 3/2002 | Ronnberg et al. |
| 2002/0035354 A1 | 3/2002 | Mirle et al. |
| 2002/0062113 A1 | 5/2002 | Thomas et al. |
| 2002/0064639 A1 | 5/2002 | Rearick et al. |
| 2002/0087136 A1 | 7/2002 | Widlund |
| 2002/0090511 A1 | 7/2002 | Smith et al. |
| 2002/0110672 A1 | 8/2002 | Muratore-Pallatino et al. |
| 2002/0123728 A1 | 9/2002 | Graef et al. |
| 2002/0133132 A1 | 9/2002 | Copat et al. |
| 2002/0150678 A1 | 10/2002 | Cramer et al. |
| 2002/0165509 A1 | 11/2002 | Baer et al. |
| 2002/0176964 A1 | 11/2002 | Koslow |
| 2002/0177831 A1 | 11/2002 | Daley et al. |
| 2002/0180092 A1 | 12/2002 | Abba et al. |
| 2002/0183704 A1 | 12/2002 | Fields et al. |
| 2003/0045707 A1 | 3/2003 | West et al. |
| 2003/0050617 A1 | 3/2003 | Chen et al. |
| 2003/0070780 A1 | 4/2003 | Chen et al. |
| 2003/0073967 A1 | 4/2003 | Wahlstrom et al. |
| 2003/0088229 A1 | 5/2003 | Baker et al. |
| 2003/0088231 A1 | 5/2003 | Yoshimasa et al. |
| 2003/0093044 A1 | 5/2003 | Wahlstrom et al. |
| 2003/0097101 A1 | 5/2003 | Schmidt et al. |
| 2003/0097105 A1 | 5/2003 | Chen et al. |
| 2003/0097113 A1 | 5/2003 | Molee |
| 2003/0105442 A1 | 6/2003 | Johnston et al. |
| 2003/0114816 A1 | 6/2003 | Underhill et al. |
| 2003/0114818 A1 | 6/2003 | Benecke et al. |
| 2003/0114821 A1 | 6/2003 | Underhill et al. |
| 2003/0120249 A1 | 6/2003 | Wulz et al. |
| 2003/0121588 A1 | 7/2003 | Pargass et al. |
| 2003/0124311 A1 | 7/2003 | Cree et al. |
| 2003/0125646 A1 | 7/2003 | Whitlock |
| 2003/0134559 A1 | 7/2003 | Delzer et al. |
| 2003/0135177 A1 | 7/2003 | Baker |
| 2003/0150551 A1 | 8/2003 | Baker |
| 2003/0157857 A1 | 8/2003 | Cook et al. |
| 2003/0171729 A1 | 9/2003 | Kaun et al. |
| 2003/0180341 A1 | 9/2003 | Gooch et al. |
| 2003/0208175 A1 | 11/2003 | Gross et al. |
| 2003/0212359 A1 | 11/2003 | Butler |
| 2003/0225383 A1 | 12/2003 | Glaug et al. |
| 2004/0019338 A1 | 1/2004 | Litvay et al. |
| 2004/0019339 A1 | 1/2004 | Ranganathan et al. |
| 2004/0019340 A1 | 1/2004 | McBride |
| 2004/0019342 A1 | 1/2004 | Nagasuna et al. |
| 2004/0024375 A1 | 2/2004 | Litvay |
| 2004/0033750 A1 | 2/2004 | Everett et al. |
| 2004/0054343 A1 | 3/2004 | Barnett et al. |
| 2004/0054344 A1 | 3/2004 | Roettger et al. |
| 2004/0057855 A1 | 3/2004 | Gerlach et al. |
| 2004/0065420 A1 | 4/2004 | Graef et al. |
| 2004/0078016 A1 | 4/2004 | Baker |
| 2004/0087927 A1 | 5/2004 | Suzuki |
| 2004/0111074 A1 | 6/2004 | Eliasson |
| 2004/0127862 A1 | 7/2004 | Bubb et al. |
| 2004/0177935 A1 | 9/2004 | Hamed et al. |
| 2004/0181199 A1 | 9/2004 | Moberg-Alehammar et al. |
| 2004/0204696 A1 | 10/2004 | Chen |
| 2004/0230173 A1 | 11/2004 | Barge et al. |
| 2004/0230184 A1 | 11/2004 | Babusik et al. |
| 2004/0243042 A1 | 12/2004 | Lipman |
| 2004/0243080 A1 | 12/2004 | Baer |
| 2004/0243081 A1 | 12/2004 | Suzuki et al. |
| 2004/0253894 A1 | 12/2004 | Fell et al. |
| 2004/0254552 A1 | 12/2004 | Mangold |
| 2005/0008825 A1 | 1/2005 | Casey et al. |
| 2005/0013992 A1 | 1/2005 | Azad et al. |
| 2005/0049566 A1 | 3/2005 | Vukos et al. |
| 2005/0079361 A1 | 4/2005 | Hamed et al. |
| 2005/0096616 A1 | 5/2005 | Arora et al. |
| 2005/0112979 A1 | 5/2005 | Sawyer et al. |
| 2005/0119631 A1 | 6/2005 | Giloh et al. |
| 2005/0136773 A1 | 6/2005 | Yahiaoui et al. |
| 2005/0165371 A1 | 7/2005 | Giacometti |
| 2005/0215965 A1 | 9/2005 | Schmidt et al. |
| 2005/0215967 A1 | 9/2005 | Toro et al. |
| 2005/0222547 A1 | 10/2005 | Beruda et al. |
| 2005/0228353 A1 | 10/2005 | Thomas |
| 2005/0261649 A1 | 11/2005 | Cohen |
| 2005/0267429 A1 | 12/2005 | Cohen |
| 2006/0009744 A1 | 1/2006 | Edrman et al. |
| 2006/0020250 A1 | 1/2006 | Chester et al. |
| 2006/0058750 A1 | 3/2006 | Di Girolamo et al. |
| 2006/0069366 A1 | 3/2006 | Cole |
| 2006/0069367 A1 | 3/2006 | Waksmundzki et al. |
| 2006/0069375 A1 | 3/2006 | Waksmundzki et al. |
| 2006/0122548 A1 | 6/2006 | Abrams |
| 2006/0122572 A1 | 6/2006 | Suarez |
| 2006/0153904 A1 | 7/2006 | Smith et al. |
| 2006/0161122 A1 | 7/2006 | Erdman et al. |
| 2006/0178650 A1 | 8/2006 | Hakannsson et al. |
| 2006/0184147 A1 | 8/2006 | Hamed |
| 2006/0206047 A1 | 9/2006 | Lampe et al. |
| 2006/0206073 A1 | 9/2006 | Crane et al. |
| 2006/0206074 A1 | 9/2006 | Bernal et al. |
| 2006/0282028 A1 | 12/2006 | Howard et al. |
| 2007/0003604 A1 | 1/2007 | Jones |
| 2007/0040454 A1 | 2/2007 | Freudenberger et al. |
| 2007/0055209 A1 | 3/2007 | Patel et al. |
| 2007/0073254 A1 | 3/2007 | Ponomarenko et al. |
| 2007/0100308 A1 | 5/2007 | Miyairi |
| 2007/0167096 A1 | 7/2007 | Scott |
| 2007/0167884 A1 | 7/2007 | Mangrum et al. |
| 2007/0224903 A1 | 9/2007 | Chakravarty et al. |
| 2007/0225663 A1 | 9/2007 | Watt et al. |
| 2007/0254550 A1 | 11/2007 | Hamed et al. |
| 2007/0270070 A1 | 11/2007 | Hamed |
| 2008/0004581 A1 | 1/2008 | Babusik et al. |
| 2008/0015532 A1 | 1/2008 | Waksmundzki |
| 2008/0031748 A1 | 2/2008 | Ihle et al. |
| 2008/0082075 A1 | 4/2008 | Morrell-Schwartz |
| 2008/0090050 A1 | 4/2008 | Seyler et al. |
| 2008/0114317 A1 | 5/2008 | Seyler |
| 2008/0119586 A1 | 5/2008 | Byerly et al. |
| 2008/0132821 A1 | 6/2008 | Propp et al. |
| 2008/0147024 A1 | 6/2008 | Potts et al. |
| 2008/0243100 A1 | 10/2008 | Wu et al. |
| 2008/0255533 A1 | 10/2008 | Wu et al. |
| 2008/0306456 A1 | 12/2008 | Riesinger |
| 2008/0312621 A1 | 12/2008 | Hundorf et al. |
| 2008/0312622 A1 | 12/2008 | Hundorf et al. |
| 2009/0062760 A1 | 3/2009 | Wright et al. |
| 2009/0076472 A1 | 3/2009 | Goldwasser et al. |
| 2009/0112175 A1 | 4/2009 | Bissah et al. |
| 2009/0125004 A1 | 5/2009 | Shen et al. |
| 2009/0157024 A1 | 6/2009 | Song |
| 2009/0204087 A1 | 8/2009 | Herfert et al. |
| 2009/0216168 A1 | 8/2009 | Eckstein et al. |
| 2009/0234306 A1 | 9/2009 | Vitaris |

(56) References Cited

U.S. PATENT DOCUMENTS

| | | |
|---|---|---|
| 2009/0299251 A1 | 12/2009 | Buan |
| 2009/0299255 A1 | 12/2009 | Kazala, Jr. et al. |
| 2009/0299306 A1 | 12/2009 | Buan |
| 2010/0010461 A1 | 1/2010 | Herfert et al. |
| 2010/0030171 A1 | 2/2010 | Canada et al. |
| 2010/0036342 A1 | 2/2010 | Carlucci et al. |
| 2010/0048072 A1 | 2/2010 | Kauscheke et al. |
| 2010/0055158 A1 | 3/2010 | Vitaris et al. |
| 2010/0069858 A1 | 3/2010 | Olson |
| 2010/0106120 A1 | 4/2010 | Holm |
| 2010/0121298 A1 | 5/2010 | Seyler et al. |
| 2010/0125258 A1 | 5/2010 | Coulthard et al. |
| 2010/0168695 A1 | 7/2010 | Robles et al. |
| 2010/0217177 A1 | 8/2010 | Cali et al. |
| 2010/0256545 A1 | 10/2010 | Aali et al. |
| 2010/0256584 A1 | 10/2010 | Litvay |
| 2010/0256586 A1 | 10/2010 | Bergstrom et al. |
| 2010/0259406 A1 | 10/2010 | Caso et al. |
| 2010/0262091 A1 | 10/2010 | Larsson |
| 2010/0305526 A1 | 12/2010 | Robinson et al. |
| 2010/0318047 A1 | 12/2010 | Ducker et al. |
| 2010/0318052 A1 | 12/2010 | Ha et al. |
| 2010/0324516 A1 | 12/2010 | Braga et al. |
| 2011/0004172 A1 | 1/2011 | Eckstein et al. |
| 2011/0034892 A1 | 2/2011 | Buan |
| 2011/0052664 A1 | 3/2011 | Tennican et al. |
| 2011/0059329 A1 | 3/2011 | Dobrawa et al. |
| 2011/0060303 A1 | 3/2011 | Bissah et al. |
| 2011/0118683 A1 | 5/2011 | Weston |
| 2011/0125119 A1 | 5/2011 | Weismantel et al. |
| 2011/0137222 A1 | 6/2011 | Masini |
| 2011/0152813 A1 | 6/2011 | Ellingson |
| 2011/0178375 A1 | 7/2011 | Forster |
| 2011/0183109 A1 | 7/2011 | Seyler et al. |
| 2011/0184364 A1 | 7/2011 | Biggs et al. |
| 2011/0184370 A1 | 7/2011 | Seyler et al. |
| 2011/0208145 A1 | 8/2011 | Zhang et al. |
| 2011/0213286 A1 | 9/2011 | Riesinger |
| 2011/0218509 A1 | 9/2011 | Dontas |
| 2011/0223413 A1 | 9/2011 | Herfert et al. |
| 2011/0224631 A1 | 9/2011 | Simmons |
| 2011/0238026 A1 | 9/2011 | Zhang et al. |
| 2011/0245788 A1 | 10/2011 | Canada |
| 2011/0247636 A1 | 10/2011 | Pollack |
| 2011/0257572 A1 | 10/2011 | Locke et al. |
| 2011/0268932 A1 | 11/2011 | Catalan et al. |
| 2012/0004632 A1 | 1/2012 | Zhang et al. |
| 2012/0041402 A1 | 2/2012 | Greener |
| 2012/0045639 A1 | 2/2012 | Whitmore et al. |
| 2012/0051945 A1 | 3/2012 | Orndorff et al. |
| 2012/0053547 A1 | 3/2012 | Schroeder et al. |
| 2012/0065664 A1 | 3/2012 | Avitable et al. |
| 2012/0071848 A1 | 3/2012 | Zhang et al. |
| 2012/0095380 A1 | 4/2012 | Gergley et al. |
| 2012/0095426 A1 | 4/2012 | Visscher et al. |
| 2012/0101465 A1 | 4/2012 | Mcguire, Jr. |
| 2012/0123311 A1 | 5/2012 | Weidemann-Hendrickson et al. |
| 2012/0136329 A1 | 5/2012 | Carney |
| 2012/0143158 A1 | 6/2012 | Yang et al. |
| 2012/0165765 A1 | 6/2012 | Barta et al. |
| 2012/0172778 A1 | 7/2012 | Rastegar et al. |
| 2012/0197229 A1 | 8/2012 | Buan |
| 2012/0203145 A1 | 8/2012 | Nilsson |
| 2012/0203189 A1 | 8/2012 | Barta et al. |
| 2012/0220968 A1 | 8/2012 | Confalone et al. |
| 2012/0238932 A1 | 9/2012 | Atteia et al. |
| 2012/0302440 A1 | 11/2012 | Theliander et al. |
| 2012/0308780 A1 | 12/2012 | Rottger et al. |
| 2012/0310186 A1 | 12/2012 | Moghe et al. |
| 2012/0310197 A1 | 12/2012 | Thomas |
| 2012/0330253 A1 | 12/2012 | Robinson et al. |
| 2013/0012902 A1 | 1/2013 | Rovaniemi |
| 2013/0066285 A1 | 3/2013 | Locke et al. |
| 2013/0066289 A1 | 3/2013 | Song et al. |
| 2013/0090616 A1 | 4/2013 | Neubauer |
| 2013/0116635 A1 | 5/2013 | Fleischmann |
| 2013/0138054 A1 | 5/2013 | Fleischmann |
| 2013/0144227 A1 | 6/2013 | Locke et al. |
| 2013/0144230 A1 | 6/2013 | Wu et al. |
| 2013/0150814 A1 | 6/2013 | Buan |
| 2013/0165878 A1 | 6/2013 | Heagle |
| 2013/0190705 A1 | 7/2013 | Vess et al. |
| 2013/0274688 A1 | 10/2013 | Weston |
| 2013/0296762 A1 | 11/2013 | Toth |
| 2013/0302545 A1 | 11/2013 | Schnelker et al. |
| 2013/0310781 A1 | 11/2013 | Phillips et al. |
| 2013/0331822 A1 | 12/2013 | Patel et al. |
| 2014/0024989 A1 | 1/2014 | Ueda |
| 2014/0094730 A1 | 4/2014 | Greener |
| 2014/0114268 A1 | 4/2014 | Auguste et al. |
| 2014/0200533 A1 | 7/2014 | Whyte et al. |
| 2014/0228791 A1 | 8/2014 | Hartwell |
| 2014/0316359 A1 | 10/2014 | Collinson et al. |
| 2015/0032035 A1 | 1/2015 | Banwell et al. |
| 2015/0119831 A1 | 4/2015 | Robinson et al. |
| 2015/0119832 A1 | 4/2015 | Locke |
| 2015/0119833 A1 | 4/2015 | Coulthard et al. |
| 2015/0159066 A1 | 6/2015 | Hartwell et al. |
| 2015/0182677 A1 | 7/2015 | Collinson et al. |
| 2015/0190286 A1 | 7/2015 | Allen et al. |
| 2015/0216733 A1 | 8/2015 | Allen et al. |
| 2015/0308994 A1 | 10/2015 | Hammond et al. |
| 2015/0320602 A1 | 11/2015 | Locke et al. |
| 2016/0000611 A1 | 1/2016 | Niederauer et al. |
| 2016/0136339 A1 | 5/2016 | Begin et al. |
| 2016/0144084 A1 | 5/2016 | Collinson et al. |
| 2016/0298620 A1 | 10/2016 | Cordoba et al. |
| 2016/0317357 A1 | 11/2016 | Vitaris et al. |
| 2017/0007751 A1 | 1/2017 | Hartwell et al. |
| 2017/0128642 A1 | 5/2017 | Buan |
| 2017/0181896 A1 | 6/2017 | Hartwell |
| 2017/0181897 A1 | 6/2017 | Hartwell |
| 2017/0368239 A1 | 12/2017 | Askem et al. |
| 2018/0133378 A1 | 5/2018 | Askem et al. |
| 2018/0221211 A1 | 8/2018 | Luckemeyer et al. |
| 2018/0235646 A1 | 8/2018 | Locke et al. |
| 2018/0296397 A1 | 10/2018 | Askem et al. |
| 2018/0318476 A1 | 11/2018 | Askem et al. |
| 2019/0240385 A1 | 8/2019 | Hartwell et al. |
| 2020/0121833 A9 | 4/2020 | Askem et al. |
| 2020/0139023 A1 | 5/2020 | Haggstrom et al. |

FOREIGN PATENT DOCUMENTS

| | | |
|---|---|---|
| CN | 103405846 | 11/2013 |
| DE | 34 43 101 | 5/1986 |
| DE | 20 2004 017 052 | 7/2005 |
| EP | 0 257 916 | 3/1988 |
| EP | 0 340 018 | 11/1989 |
| EP | 0392640 A2 | 10/1990 |
| EP | 0630629 A1 | 12/1994 |
| EP | 0 549 781 | 9/1996 |
| EP | 0 748 894 | 12/1996 |
| EP | 0 599 871 | 4/1997 |
| EP | 0 875 224 | 11/1998 |
| EP | 0 941 726 | 9/1999 |
| EP | 1 013 290 | 6/2000 |
| EP | 1 048 278 | 11/2000 |
| EP | 1 066 809 | 1/2001 |
| EP | 1 139 951 | 10/2001 |
| EP | 1 312 328 | 5/2003 |
| EP | 1 452 156 | 9/2004 |
| EP | 1 476 217 | 3/2008 |
| EP | 1 955 887 | 8/2008 |
| EP | 2 161 011 | 3/2010 |
| EP | 2 263 627 | 12/2010 |
| EP | 2 366 721 | 9/2011 |
| EP | 2 021 046 | 3/2012 |
| EP | 2 462 908 | 6/2012 |
| EP | 2 529 767 | 12/2012 |
| EP | 2 544 642 | 1/2015 |
| EP | 2 648 668 | 1/2015 |
| FR | 1 163 907 | 10/1958 |
| GB | 1255395 | 12/1971 |

(56) References Cited

FOREIGN PATENT DOCUMENTS

| | | |
|---|---|---|
| GB | 2355228 | 4/2001 |
| GB | 2435422 | 8/2007 |
| GB | 2435423 | 8/2007 |
| GB | 2489947 | 10/2012 |
| GB | 2496310 | 5/2013 |
| JP | 2014-168573 | 9/2014 |
| KR | 101333344 B1 | 11/2013 |
| WO | WO 1983/00742 | 3/1983 |
| WO | WO 1991/11161 | 8/1991 |
| WO | WO 1991/11162 | 8/1991 |
| WO | WO 1993/01778 | 2/1993 |
| WO | WO 1993/01779 | 2/1993 |
| WO | WO 1993/01780 | 2/1993 |
| WO | WO 1993/01781 | 2/1993 |
| WO | WO 1993/09745 | 5/1993 |
| WO | WO 1993/11726 | 6/1993 |
| WO | WO 1994/023677 | 10/1994 |
| WO | WO 1995/13042 | 5/1995 |
| WO | WO 1995/13776 | 5/1995 |
| WO | WO 1995/13779 | 5/1995 |
| WO | WO 1995/014451 | 6/1995 |
| WO | WO 1995/16424 | 6/1995 |
| WO | WO 1995/029959 | 11/1995 |
| WO | WO 1996/005873 | 2/1996 |
| WO | WO 1996/07783 | 3/1996 |
| WO | WO 1997/11658 | 4/1997 |
| WO | WO 1997/14384 | 4/1997 |
| WO | WO 1998/20916 | 5/1998 |
| WO | WO 1998/22279 | 5/1998 |
| WO | WO 1999/04830 | 2/1999 |
| WO | WO 1999/39671 | 8/1999 |
| WO | WO 1999/45876 | 9/1999 |
| WO | WO 1999/45878 | 9/1999 |
| WO | WO 1999/56687 | 11/1999 |
| WO | WO 2000/00016 | 1/2000 |
| WO | WO 2000/00127 | 1/2000 |
| WO | WO 2000/00129 | 1/2000 |
| WO | WO 2000/000130 | 1/2000 |
| WO | WO 2000/00131 | 1/2000 |
| WO | WO 2000/040190 | 7/2000 |
| WO | WO 2000/42957 | 7/2000 |
| WO | WO 2000/059438 | 10/2000 |
| WO | WO 2001/072251 | 10/2001 |
| WO | WO 2001/090465 | 11/2001 |
| WO | WO 2002/17840 | 3/2002 |
| WO | WO 2002/024132 | 3/2002 |
| WO | WO 2002/026180 | 4/2002 |
| WO | WO 2002/076379 | 10/2002 |
| WO | WO 2003/073971 | 9/2003 |
| WO | WO 2004/043321 | 5/2004 |
| WO | WO 2004/077387 | 9/2004 |
| WO | WO 2004/098474 | 11/2004 |
| WO | WO 2005/025447 | 3/2005 |
| WO | WO 2005/123170 | 12/2005 |
| WO | WO 2006/052839 | 5/2006 |
| WO | WO 2006/105305 | 10/2006 |
| WO | WO 2007/035038 | 3/2007 |
| WO | WO 2007/040606 | 4/2007 |
| WO | WO 2007/077214 | 7/2007 |
| WO | WO 2007/077216 | 7/2007 |
| WO | WO 2007/116347 | 10/2007 |
| WO | WO 2008/039223 | 4/2008 |
| WO | WO 2009/066105 | 5/2009 |
| WO | WO 2009/124100 | 10/2009 |
| WO | WO 2009/146441 | 12/2009 |
| WO | WO 2009/152021 | 12/2009 |
| WO | WO 2009/158128 | 12/2009 |
| WO | WO 2010/032951 | 3/2010 |
| WO | WO 2010/082872 | 7/2010 |
| WO | WO-2010075180 A2 | 7/2010 |
| WO | WO 2010/089448 | 8/2010 |
| WO | WO 2010/139926 | 12/2010 |
| WO | WO 2010/142959 | 12/2010 |
| WO | WO 2011/023650 | 3/2011 |
| WO | WO 2011/058311 | 5/2011 |
| WO | WO 2011/113728 | 9/2011 |
| WO | WO 2011/128651 | 10/2011 |
| WO | WO 2011/135285 | 11/2011 |
| WO | WO 2011/135286 | 11/2011 |
| WO | WO 2011/135287 | 11/2011 |
| WO | WO 2011/144888 | 11/2011 |
| WO | WO 2011/152368 | 12/2011 |
| WO | WO 2012/035787 | 3/2012 |
| WO | WO 2012/041296 | 4/2012 |
| WO | WO 2012/074512 | 6/2012 |
| WO | WO 2012/106590 | 8/2012 |
| WO | WO 2012/131237 | 10/2012 |
| WO | WO 2012/140378 | 10/2012 |
| WO | WO 2012/143665 | 10/2012 |
| WO | WO 2012/150235 | 11/2012 |
| WO | WO 2012/168298 | 12/2012 |
| WO | WO 2013/010907 | 1/2013 |
| WO | WO 2013/014317 | 1/2013 |
| WO | WO 2013/029652 | 3/2013 |
| WO | WO 2013/060732 | 5/2013 |
| WO | WO 2013/064852 | 5/2013 |
| WO | WO 2013/083800 | 6/2013 |
| WO | WO 2013/090810 | 6/2013 |
| WO | WO 2013/136181 | 9/2013 |
| WO | WO 2013/149078 | 10/2013 |
| WO | WO 2014/008348 | 1/2014 |
| WO | WO 2014/014922 | 1/2014 |
| WO | WO 2014/016759 | 1/2014 |
| WO | WO 2014/020440 | 2/2014 |
| WO | WO 2014/020443 | 2/2014 |
| WO | WO 2014/108476 | 7/2014 |
| WO | WO 2014/113253 | 7/2014 |
| WO | WO 2015/022334 | 2/2015 |
| WO | WO 2015/022340 | 2/2015 |
| WO | WO 2015/031216 | 3/2015 |
| WO | WO 2015/110410 | 7/2015 |
| WO | WO 2015/130608 | 9/2015 |
| WO | WO 2016/018448 | 2/2016 |
| ZA | 9605526 | 2/1997 |

OTHER PUBLICATIONS

U.S. Appl. No. 61/829,187, filed May 30, 2013, Collinson et al.
U.S. Appl. No. 61/906,865, filed Nov. 20, 2013, Collinson et al.
U.S. Appl. No. 61/907,350, filed Nov. 21, 2013, Collinson et al.
"Technology Watch", May 1989, in 1 page.
Hersle, K. et al., "Uses of Dextranomer Absorbent Pads After Cryosurgery of Cutaneous Malignancies", The Journal of Dermatologic Surgery and Oncology, vol. 8, Jan. 1982, in 4 pages.
International Search Report and Written Opinion, re PCT Application No. PCT/EP2015/063373, dated Sep. 2, 2015.
International Preliminary Report on Patentability, re PCT Application No. PCT/EP2015/063373, dated Dec. 29, 2016.
International Search Report and Written Opinion, re PCT Application No. PCT/GB2014/050786, dated Jun. 12, 2014.
International Search Report, re PCT Application No. PCT/EP2014/071510, dated Feb. 5, 2015.
International Preliminary Report for Patentability, re PCT Application No. PCT/EP2014/071510, dated Apr. 21, 2016.
International Search Report and Written Opinion, re PCT Application No. PCT/EP2014/071520, dated Feb. 5, 2015.
Kendall ULTEC Hydrocolloid Dressing (4"x4'), product ordering page, web page downloaded Jul. 13, 2014, in 1 page.
Advantec MFS, Inc., "Membrane Filters" (catalog), accessed Jan. 29, 2016 (publication date unknown, but believed to be copyright 2001-2011), in 17 pages. URL: http://www.advantecmfs.com/catalog/filt/membrane.pdf#page=11.
Protz, K., "Moderne Wundauflagen unterstutzen Heilungsprozess", Wundversorgung: Indikation und Anwendung, Geriatrie Journal, Apr. 2005, pp. 3333-3339, with translation, in 17 pages.
Smith & Nephew, "PICO Single Use Negative Pressure Wound Therapy System", spiral booklet, Mar. 2011, in 7 pages.
SNAP—BLUE Foam Dressing—color brochure (L22162 rev. 130429), Jun. 2013, in 2 pages.
SNAP—Product Overview—Wound Care System, as captured on Wayback Machine on Nov. 17, 2011.

WOUND DRESSING AND METHOD OF TREATMENT

CROSS-REFERENCE TO RELATED APPLICATIONS

This application is a continuation of U.S. patent application Ser. No. 15/319,743, filed on Dec. 16, 2016, which is a national stage application of International Patent Application No. PCT/EP2015/063373, filed on Jun. 15, 2015, titled "WOUND DRESSING AND METHOD OF TREATMENT," which claims priority to U.S. Provisional Application Ser. No. 62/013989 filed on Jun. 18, 2014, titled "WOUND DRESSING AND METHOD OF TREATMENT," and U.S. Provisional Application Ser. No. 62/085774, filed on Dec. 1, 2014, titled "WOUND DRESSING AND METHOD OF TREATMENT."

FIELD OF THE INVENTION

Embodiments described herein relate to apparatuses, systems, and methods the treatment of wounds, for example using dressings in combination with negative pressure wound therapy.

SUMMARY OF THE INVENTION

Certain embodiments disclosed herein relate to improved wound dressings that exhibit enhanced visibility for underlying patient tissue. Such dressings may have advantages over prior art dressings, through which assessment of the condition of a tissue site underlying the dressing is difficult or not possible. Also disclosed are improved methods of use and systems for use of the same, preferably in conjunction with negative pressure wound therapy.

In one embodiment, an apparatus for negative pressure wound therapy comprises:
  a wound dressing comprising:
    a material layer comprising one or more through holes extending vertically through a thickness of the material layer; and
    a transparent or translucent cover layer positioned above the absorbent layer, the cover layer configured to form a negative pressure chamber underneath the cover layer; and
  a port configured to communicate negative pressure to the negative pressure chamber;
  wherein the one or more through holes in the material layer permit viewing of tissue beneath the wound dressing through the wound cover when the wound dressing is applied to a patient.

In some embodiments, the wound dressing comprises one or more lower layers beneath the material layer, wherein the through holes in the material layer permit viewing of tissue beneath the wound dressing through the wound cover and through the one or more lower layers when the wound dressing is applied to a patient. The one or more lower layers may comprise one or more transparent or translucent layers. The one or more lower layers may comprise a lower layer comprising one or more through holes extending vertically through a thickness of the lower layer. At least some of the vertically extending through holes in the lower layer may be positioned underneath at least some of the vertically extending through holes in the material layer. The vertically extending through holes in the lower layer may be smaller than the vertically extending through holes in the material layer. The one or more lower layers may comprise a tissue contact layer and a transmission layer over the tissue contact layer. The material layer may be an absorbent layer.

Some or all of the through holes in the material layer and in any lower layer may be circular in shape. Some or all of the through holes in the material layer and in any lower layer may be hexagonal in shape. Some or all of the through holes in the material layer and in any lower layer may be diamond-shaped. In some embodiments the apparatus may further comprise a filter in or below the port to retain wound exudate underneath the cover layer. The apparatus may further comprise a fluid collection canister for storage of fluids transported from the wound dressing. The port may be attached over a hole in the cover layer. The apparatus may further comprise a conduit connected to the port configured to supply negative pressure to the wound dressing. The apparatus may further comprise a source of negative pressure configured to supply negative pressure to the wound dressing.

In some embodiments, the wound dressing may further comprise a plug material positioned within at least some of the one or more through holes. The plug material may prevent or minimize suction blisters forming in the tissue underneath the at least some of the one or more through holes. The plug material may comprise a soft, transparent material. The plug material may comprise a soft, transparent, and hydrophobic material. The plug material may comprise silicone. In some embodiments, the one or more through holes can be configured to prevent or minimize suction blisters to the tissue by having a limited diameter. The limited diameter can be less than or equal to approximately 10 mm.

In another embodiment, an apparatus for negative pressure wound comprises:
  a wound dressing comprising:
    a transmission layer comprising one or more through holes extending vertically through a thickness of the transmission layer;
    an absorbent layer comprising one or more through holes extending vertically through a thickness of the absorbent layer; and
    a transparent or translucent cover layer positioned above the absorbent layer, the cover layer configured to form a negative pressure chamber underneath the cover layer; and
  a port configured to communicate negative to pressure to the negative pressure chamber;
  wherein the one or more through holes in the transmission layer are positioned at least partially below the one or more through holes in the absorbent layer to permit viewing of tissue beneath the wound dressing through the wound cover when the wound dressing is applied to a patient.

In some embodiments, the transmission layer comprises a plurality of horizontally spaced apart through holes extending vertically through the thicknesss of the transmission layer, and the absorbent layer comprises a plurality of horizontally spaced apart through holes extending vertically through the thickness of the absorbent layer. The plurality of horizontally spaced apart through holes in the transmission layer may be distributed in a regularly spaced pattern across the transmission layer, and the plurality of horizontally spaced apart through holes in the absorbent layer may be distributed in a regularly spaced pattern across the absorbent layer. The plurality of horizontally spaced apart through holes in the transmission layer may be spaced apart by 10 mm (or about 10 mm) or less, and the plurality of horizontally spaced apart through holes in the absorbent layer may be spaced apart by 10 mm (or about 10 mm) or less. The plurality of horizontally spaced apart through holes in the transmission layer may be formed in a first pattern across an area of the transmission layer, and the plurality of horizontally spaced apart through holes in the absorbent layer may be formed in a second pattern across an area of the transmission layer.

In some embodiments, at least one through hole extending vertically through the thickness of the transmission layer is located below each through hole extending vertically through the thickness of the absorbent layer. Two or more through holes extending vertically through the thickness of the transmission layer may be located below each through hole extending vertically through the thickness of the absorbent layer. The through hole(s) extending vertically through the thickness of the absorbent layer may be larger in dimension than through hole(s) extending vertically through the thickness of the transmission layer. Some or all of the through holes in the transmission layer and/or the absorbent layer may be circular in shape. Some or all of the through holes in the transmission layer and/or the absorbent layer may be hexagonal in shape. Some or all of the through holes in the transmission layer and/or the absorbent layer may be diamond-shaped. T In some embodiments, the one or more through holes in the absorbent layer can have a diameter of 10 mm (or about 10 mm) or less. The one or more through holes in the transmission layer can have a diameter of 5 mm (or about 5 mm) or less. The one or more through holes in the transmission layer can have a diameter of 1 mm (or about 1 mm) or less.

In some embodiments, the apparatus may further comprise a tissue contact layer positioned below the transmission layer. The cover layer may be configured to seal around a perimeter thereof to the tissue contact layer. The tissue contact may be is configured to seal directly to a patient's tissue. The transmission layer may comprise 3D fabric. The absorbent layer may comprise a non-woven material comprising a plurality of superabsorbing particles. In some embodiments, the apparatus may further comprise a fluid collection canister for storage of fluids transported from the wound dressing.

In some embodiments, the apparatus may further comprise a filter in or below the port to retain wound exudate underneath the cover layer. The port may be attached over a hole in the cover layer. In some embodiments, the apparatus may further comprise a conduit connected to the port configured to supply negative pressure to the wound dressing. In some embodiments, the apparatus may further comprise a source of negative pressure configured to supply negative pressure to the wound dressing.

In some embodiments, the apparatus may further comprise a plug material positioned within at least some of the one or more through holes. The plug material may prevent or minimize suction blisters forming in the tissue underneath the at least some of the one or more through holes. The plug material may comprise a soft, transparent material. The plug material may comprise a soft, transparent, and hydrophobic material. The plug material may comprise silicone.

In some embodiments, the one or more through holes can be configured to prevent or minimize suction blisters to the tissue by having a limited diameter. The limited diameter can be less than or equal to approximately 10 mm.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

DETAILED DESCRIPTION OF THE PREFERRED EMBODIMENTS

Figure 1:
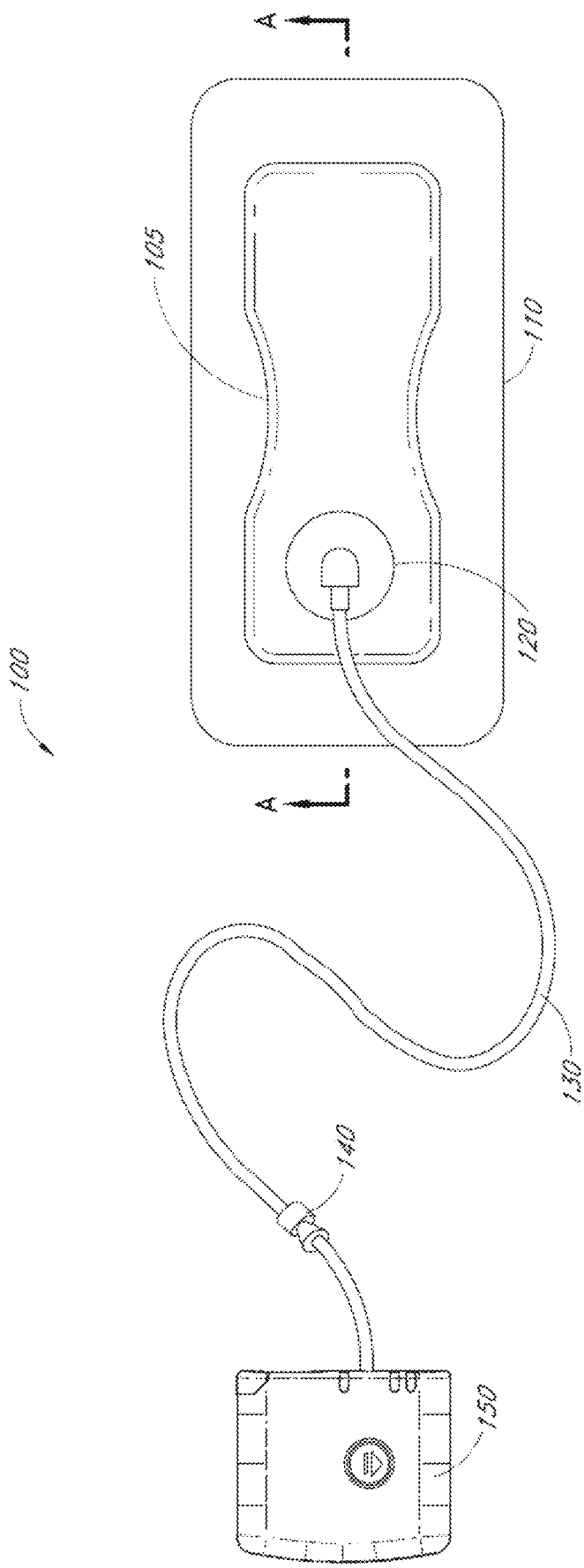
FIG. 1 illustrates an embodiment of a wound treatment system.

Embodiments disclosed herein relate to apparatuses and methods of treating a wound with reduced pressure, including pump and wound dressing components and apparatuses. The apparatuses and components comprising the wound overlay and packing materials, if any, are sometimes collectively referred to herein as dressings.

It will be appreciated that throughout this specification reference is made to a wound. It is to be understood that the term wound is to be broadly construed and encompasses open and closed wounds in which skin is torn, cut or punctured or where trauma causes a contusion, or any other superficial or other conditions or imperfections on the skin of a patient or otherwise that benefit from reduced pressure treatment. A wound is thus broadly defined as any damaged region of tissue where fluid may or may not be produced. Examples of such wounds include, but are not limited to, abdominal wounds or other large or incisional wounds, either as a result of surgery, trauma, sterniotomies, fasciotomies, or other conditions, dehisced wounds, acute wounds, chronic wounds, subacute and dehisced wounds, traumatic wounds, flaps and skin grafts, lacerations, abrasions, contusions, burns, diabetic ulcers, pressure ulcers, stoma, surgical wounds, trauma and venous ulcers or the like. Some embodiments of the dressings described herein may be used over a tissue site susceptible to form a wound or likely to form a wound, for example a tissue site over a bony prominence susceptible to forming a pressure ulcer.

It will be understood that embodiments of the present disclosure are generally applicable to use in topical negative pressure ("TNP") therapy systems. Briefly, negative pressure wound therapy assists in the closure and healing of many forms of "hard to heal" wounds by reducing tissue oedema; encouraging blood flow and granular tissue formation; removing excess exudate and may reduce bacterial load (and thus infection risk). In addition, the therapy allows for less disturbance of a wound leading to more rapid healing. TNP therapy systems may also assist on the healing of surgically closed wounds by removing fluid and by helping to stabilize the tissue in the apposed position of closure. A further beneficial use of TNP therapy can be found in grafts and flaps where removal of excess fluid is important and close proximity of the graft to tissue is required in order to ensure tissue viability.

As is used herein, reduced or negative pressure levels, such as −X mmHg, represent pressure levels that are below standard atmospheric pressure, which corresponds to 760 mmHg (or 1 atm, 29.93 inHg, 101.325 kPa, 14.696 psi, etc.). Accordingly, a negative pressure value of −X mmHg reflects absolute pressure that is X mmHg below 760 mmHg or, in other words, an absolute pressure of (760−X) mmHg. In addition, negative pressure that is "less" or "smaller" than X mmHg corresponds to pressure that is closer to atmospheric pressure (e.g., −40 mmHg is less than −60 mmHg). Negative pressure that is "more" or "greater" than −X mmHg corresponds to pressure that is further from atmospheric pressure (e.g., −80 mmHg is more than −60 mmHg).

The negative pressure range for some embodiments of the present disclosure can be approximately −80 mmHg, or between about −20 mmHg and −200 mmHg. Note that these pressures are relative to normal ambient atmospheric pressure. Thus, −200 mmHg would be about 560 mmHg in practical terms. In some embodiments, the pressure range can be between about −40 mmHg and −150 mmHg. Alternatively a pressure range of up to −75 mmHg, up to −80 mmHg or over −80 mmHg can be used. Also in other embodiments a pressure range of below −75 mmHg can be used. Alternatively, a pressure range of over approximately −100 mmHg, or even 150 mmHg, can be supplied by the negative pressure apparatus. In some embodiments of wound closure devices described here, increased wound contraction can lead to increased tissue expansion in the surrounding wound tissue. This effect may be increased by varying the force applied to the tissue, for example by varying the negative pressure applied to the wound over time, possibly in conjunction with increased tensile forces applied to the wound via embodiments of the wound closure devices. In some embodiments, negative pressure may be varied over time for example using a sinusoidal wave, square wave, and/or in synchronization with one or more patient physiological indices (e.g., heartbeat).

As used herein, the term "horizontal," when referring to a wound, indicates a direction or plane generally parallel to the skin surrounding the wound. The term "vertical," when referring to a wound, generally refers to a direction extending perpendicular to the horizontal plane. The terms "horizontal" and "vertical" may also be used to describe the components of the wound treatment system, such as layers of the wound dressing. When describing these components, these terms should not be construed to require that the structures or devices necessarily be placed into a wound in a certain orientation, though in certain embodiments, it may be preferable to do so.

I. Example Systems and Use

FIG. 1 illustrates an embodiment of a TNP wound treatment system 100 comprising a wound dressing 110 in combination with a pump 150. The wound dressing 110 can be any wound dressing embodiment disclosed herein including without limitation dressing embodiment or have any combination of features of any number of wound dressing embodiments disclosed herein. Here, the dressing 110 may be placed over a wound as described previously, and a conduit 130 may then be connected to the port 120, although in some embodiments the dressing 101 may be provided with at least a portion of the conduit 130 preattached to the port 120. Alternatively, in some embodiments the dressing 110 can be placed over a tissue site likely to form a wound, such as a pressure site likely to form a pressure ulcer. Preferably, the dressing 110 is provided as a single article with all wound dressing elements (including the port 120) pre-attached and integrated into a single unit. The wound dressing 110 may then be connected, via the conduit 130, to a source of negative pressure such as the pump 150. The pump 150 can be miniaturized and portable, although larger conventional pumps may also be used with the dressing 110. In some embodiments, the pump 150 may be attached or mounted onto or adjacent the dressing 110. A connector 140 may also be provided so as to permit the conduit 130 leading to the wound dressing 110 to be disconnected from the pump, which may be useful for example during dressing changes. Embodiments of the dressing of FIG. 1 are further described with respect to FIGS. 3A-11, which also provide additional details on the specific internal components of the dressing embodiment depicted in FIG. 1.

In some embodiments, fluid may be transported from the dressing 110 and stored in a fluid collection canister (not shown). Some embodiments, may call for fluid to be retained within the dressing such as within an absorbent material. The absorbent material may further comprise a superabsorbent polymer or a more conventional absorbent material such as cellulose.

Figure 2A:
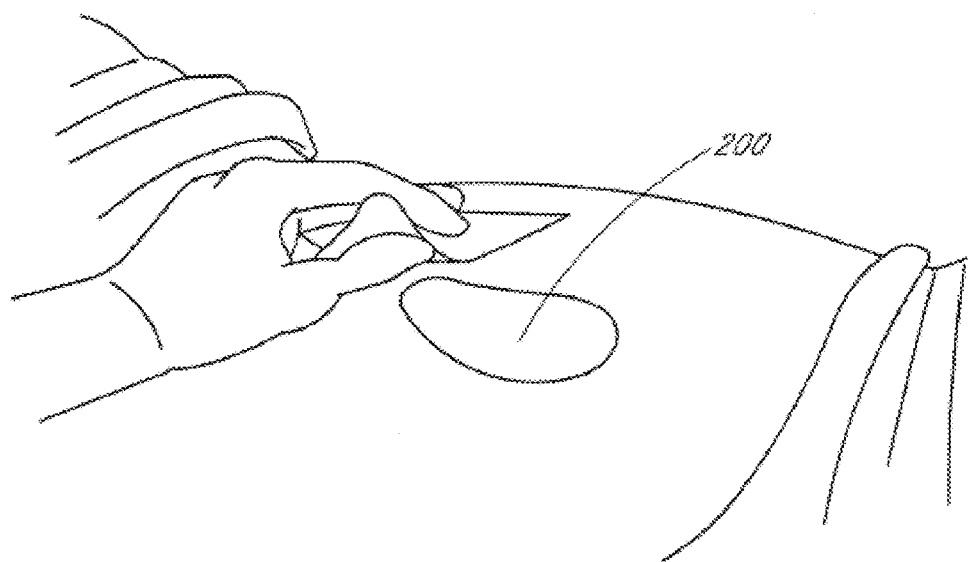
FIGS. 2A-E illustrate the use and application of an embodiment of a wound treatment system onto various wounds.

FIGS. 2A-D illustrate the use of an embodiment of a TNP wound treatment system being used to treat a wound site on a patient. FIG. 2A shows a wound site 200 being cleaned and prepared for treatment. Here, the healthy skin surrounding the wound site 200 is preferably cleaned and excess hair removed or shaved. The wound site 200 may also be irrigated with sterile saline solution if necessary. Optionally, a skin protectant may be applied to the skin surrounding the wound site 200. If necessary, a wound packing material, such as foam or gauze, may be placed in the wound site 200. This may be preferable if the wound site 200 is a deeper wound. In embodiments, the wound may be any type of wound described herein this section or elsewhere in the specification.

Figure 2B:
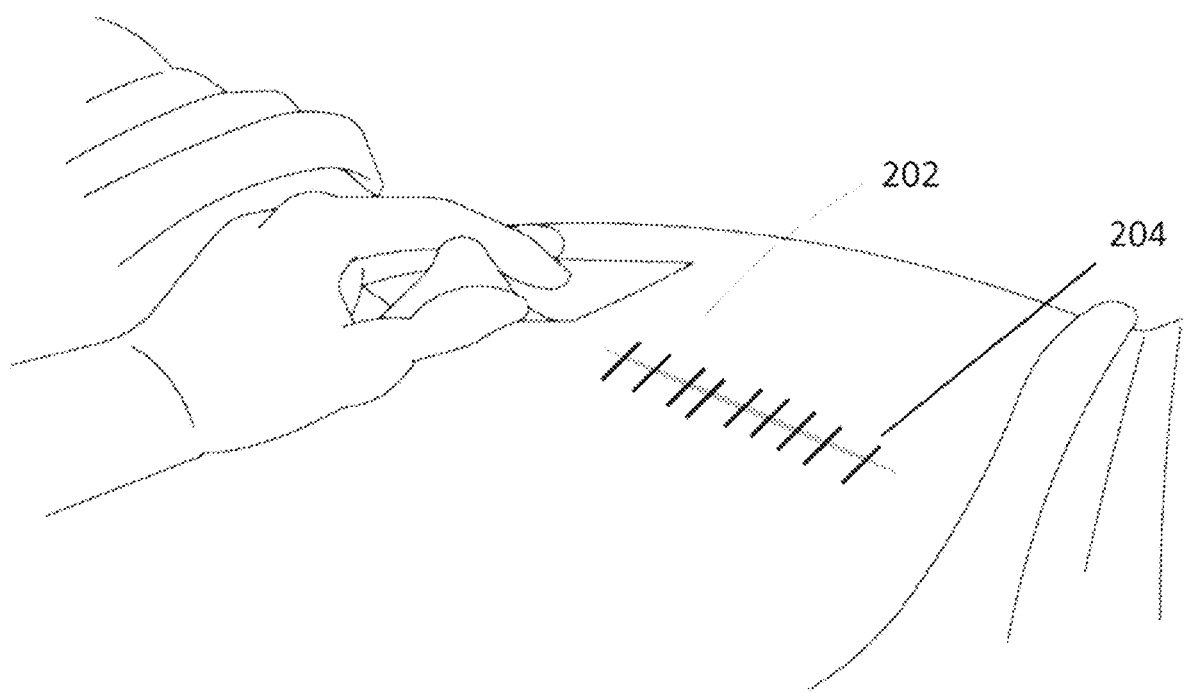

FIG. 2B illustrates an incisional wound site 202 that may be irrigated and prepared as the wound site 200 described in relation to FIG. 2A. Typical incisional wounds are created by a scalpel or other means during surgery to allow a clinician access to the underlying tissues and organs. The incisional wound 202 may be closed, whereby the wound has been closed by sutures 204 or other means such as an adhesive, or the incisional wound may be open, wherein the wound has not yet been closed. As described above, throughout this specification reference is made to a wound and such a wound may be created by a variety of means including via incisional means. Thus, it will be understood by one skilled in the art, when the term "wound" is used in describing embodiments herein this section and elsewhere in the specification, the term "wound" encompasses incisional wounds such as those described in FIG. 2B. Although not illustrated, the term "wound" also encompasses potential wound sites, such as bony prominences that may form a pressure ulcer.

Figure 2C:
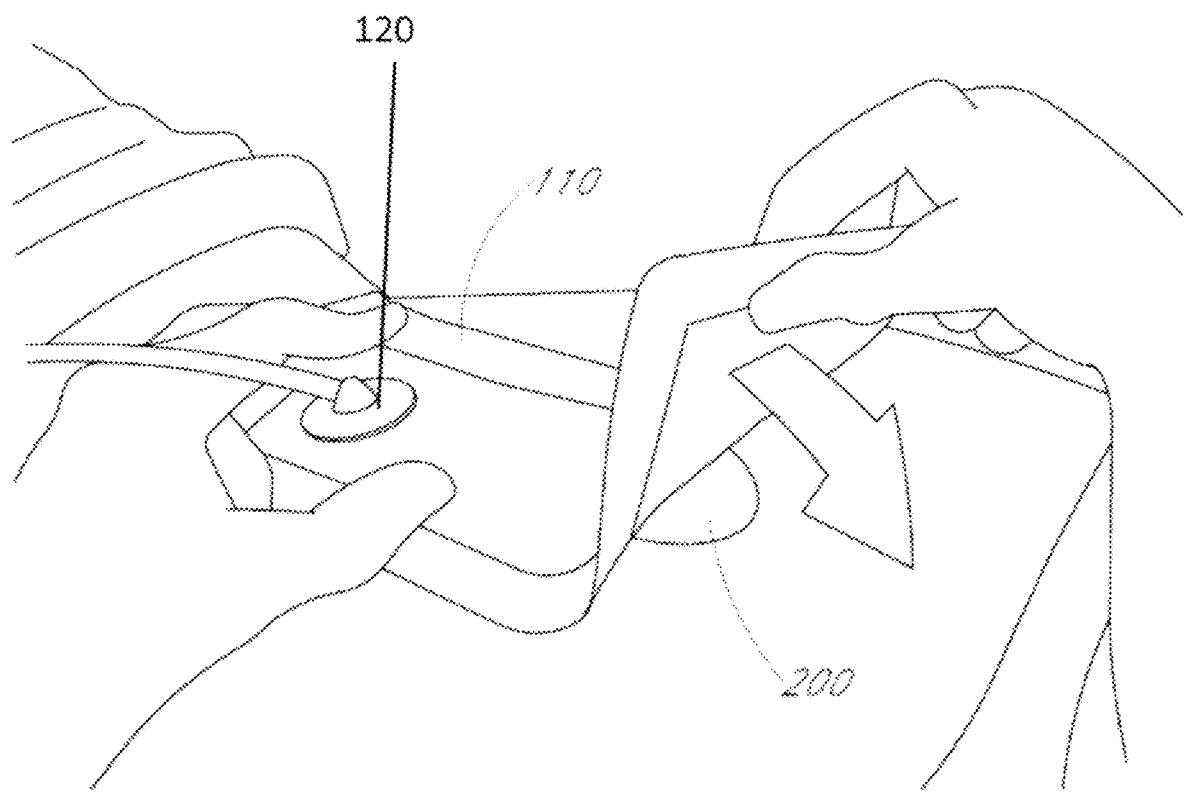

After the skin surrounding the wound site 200 is dry, and with reference now to FIG. 2C, the wound dressing 110 may be positioned and placed over the wound site 200 or 202. Preferably, the wound dressing 110 is placed over and/or in contact with the wound site 200. In some embodiments, an adhesive layer is provided on the lower surface of the dressing 110, which may in some cases be protected by an optional release layer to be removed prior to placement of the wound dressing 110 over the wound site 200. Preferably, the dressing 110 is positioned such that the port 120 is in a raised position with respect to the remainder of the dressing 110 so as to avoid fluid pooling around the port. In some embodiments, the dressing 110 is positioned so that the port 120 is not directly overlying the wound, and is level with or at a higher point than the wound. To help ensure adequate sealing for negative pressure wound therapy, the edges of the dressing 110 are preferably smoothed over to avoid creases or folds.

Figure 2D:
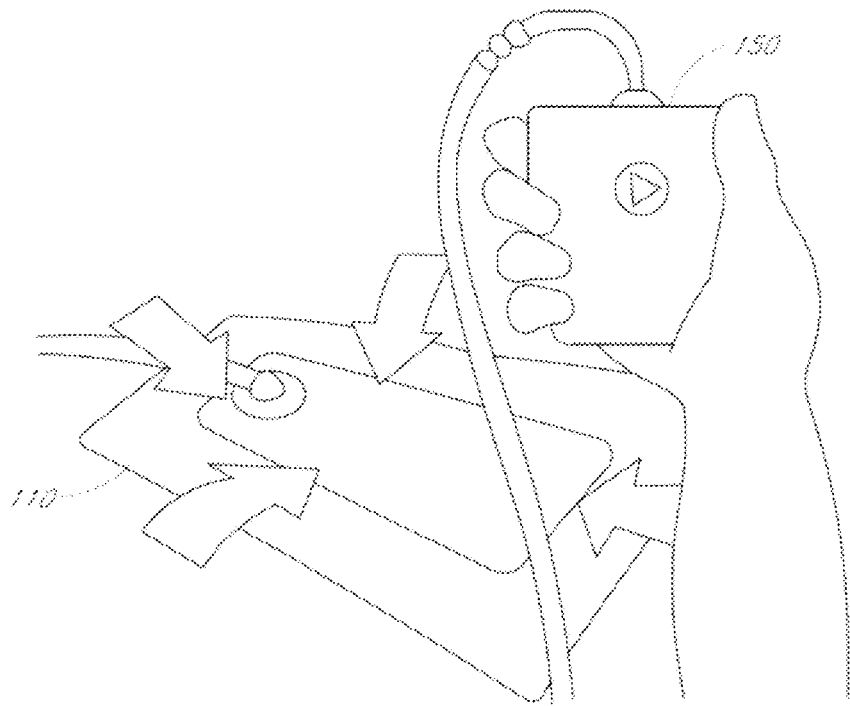

With reference now to FIG. 2D, the dressing 110 is connected to the pump 150. The pump 150 is configured to apply negative pressure to the wound site via the dressing 110, and typically through a conduit. In some embodiments, and as described above in FIG. 1, a connector may be used to join the conduit from the dressing 110 to the pump 150. Upon the application of negative pressure with the pump 150, the dressing 110 may, in some embodiments, partially collapse and present a wrinkled appearance as a result of the evacuation of some or all of the air underneath the dressing 110. In some embodiments, the pump 150 may be configured to detect if any leaks are present in the dressing 110, such as at the interface between the dressing 110 and the skin surrounding the wound site 200. Should a leak be found, such leak is preferably remedied prior to continuing treatment.

Figure 2E:
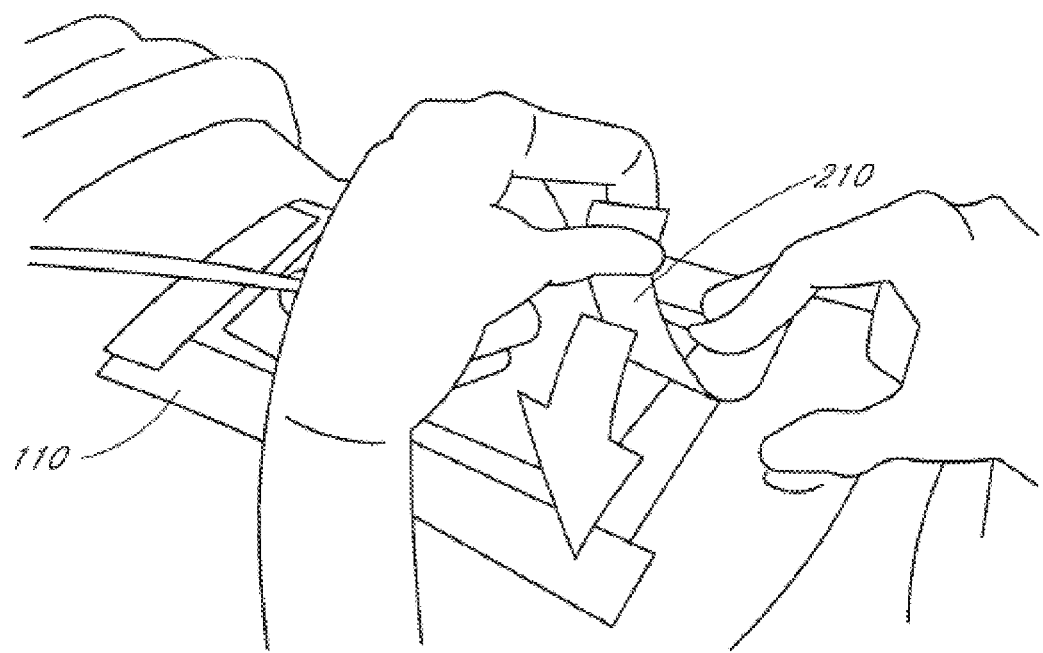

Turning to FIG. 2E, additional fixation strips 210 may also be attached around the edges of the dressing 110. Such fixation strips 210 may be advantageous in some situations so as to provide additional sealing against the skin of the patient surrounding the wound site 200. For example, the fixation strips 210 may provide additional sealing for when a patient is more mobile. In some cases, the fixation strips 210 may be used prior to activation of the pump 150, particularly if the dressing 110 is placed over a difficult to reach or contoured area.

Treatment of the wound site 200 preferably continues until the wound has reached a desired level of healing. In some embodiments, it may be desirable to replace the dressing 110 after a certain time period has elapsed, or if the dressing is full of wound fluids. During such changes, the pump 150 may be kept, with just the dressing 110 being changed.

II. Example Dressings

Figure 3A:
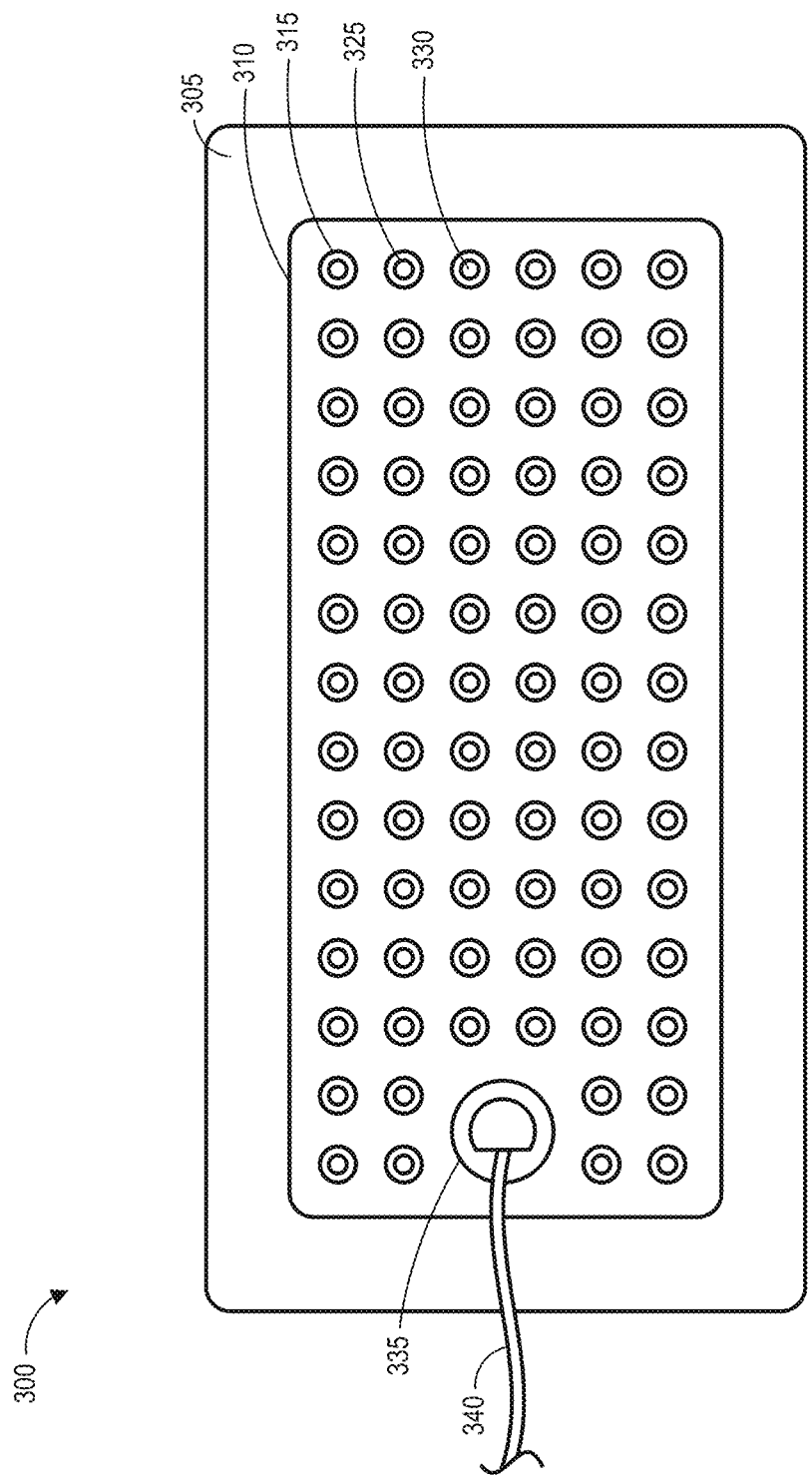
FIGS. 3A-3C illustrate an embodiment of a wound dressing configured for enhanced tissue visibility.
Figure 3B:
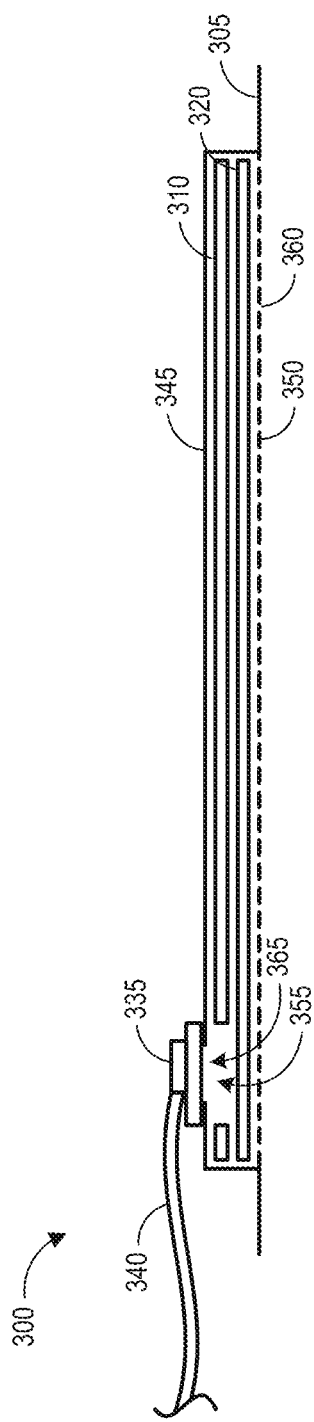
Figure 3C:
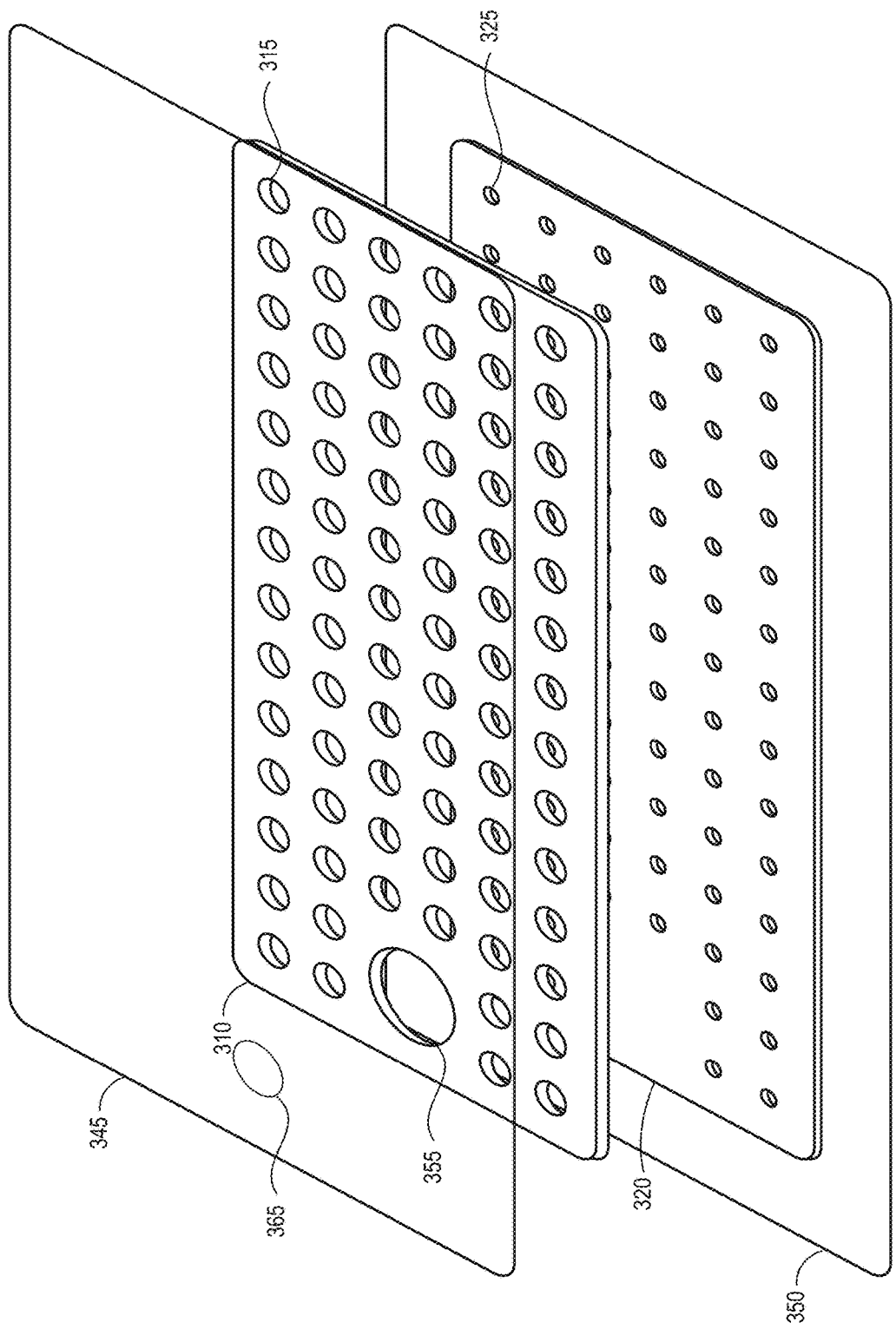

FIGS. 3A-C illustrate various views of a viewing portal wound dressing 300 that can be used in a similar system to FIG. 1 to provide visibility of underlying tissue according to an embodiment of the disclosure. In some circumstances, it can be beneficial for a clinician to be able to visually assess the quality of the tissue underlying the dressing 300. For example, a clinician can assess the progress of healing of wound tissue underlying the dressing 300 in some examples. Viewing portals 330 in the dressing 300 permit viewing of tissue beneath the wound dressing through the wound cover when the wound dressing is applied to a patient, for example allowing a clinician to view the tissue underlying the dressing to determine whether the tissue is a wound site, healthy tissue, or an infection, to name a few. In other examples, the dressing 300 can be applied as a prophylactic measure to healthy or relatively healthy skin in an area that may form a wound and the clinician may wish to monitor changes in the underlying tissue to determine whether a wound is forming. By monitoring changes in the color of the underlying tissue or for signs of the dermis breaking down, a clinician can determine whether further treatment is needed, such as debridement. For instance, the dressing 300 may be applied to a bony prominence possibly prone to forming a pressure ulcer. The dressing 300 can provide cushioning to protect the bony prominence, and the blood perfusion resulting from negative pressure applied through the dressing 300 can provide therapeutic benefits including preventing, delaying, or mitigating formation of pressure ulcers. The viewing portals 330 in the dressing 300 can allow a clinician to determine whether a wound has formed in the underlying tissue and/or determine an approximate area of an ulcer. In other examples, the dressing 300 can be applied as a prophylactic measure to reddened or bruised tissue, to tissue on pressure points such as the shoulder or buttocks of bedridden patients, or the like. The material layers of the dressing 300 can serve to transmit negative pressure to the tissue site and also absorb any initial exudate from formation of a wound. These are just a few circumstances in which a clinician may wish to monitor changes in tissue underlying a dressing 300. The clinician can use viewing portals 330 through the internal layers of the dressing to monitor tissue characteristics and changes, as discussed in more detail below.

FIG. 3A illustrates a top view of the wound dressing 300, FIG. 3B illustrates a schematic cross-sectional view of the wound dressing 300, and FIG. 3C illustrates an exploded view of various layers of the wound dressing 300. The wound dressing 300 can be located over a wound site or potentially wound-forming tissue site to be treated. The dressing 300 may be placed so as to form a sealed cavity over the wound site. In some embodiments, the dressing 300 comprises a cover layer 345 attached to an optional tissue contact layer 350, both of which are described in greater detail below. These two layers 345, 350 are preferably joined or sealed together around a perimeter 305 so as to define an interior space or chamber. The cover layer 345 can be configured to form a negative pressure chamber underneath the cover layer. The interior space or chamber may comprise additional structures that may be adapted to distribute or transmit negative pressure, store wound exudate and other fluids removed from the wound, and other functions which will be explained in greater detail below. Examples of such structures, described below, include a transmission layer 310 and/or an absorbent layer 320.

The various layers used to form the wound dressing 300 or other wound dressings described in this specification may have any of a number of perimeter shapes when viewed from above, as in FIG. 3A. For example, the layers may have a rectangular, square, elongated, elliptical, circular or other shapes. In some embodiments, each of the layers has the same or similar shape, though they may be of different sizes (as shown in FIG. 3C). FIG. 3A illustrates layers that have a rectangular shape with a length and a width extending within a horizontal plane. FIG. 3B illustrates that each of the layers may have a vertical thickness perpendicular to the horizontal dimensions of the layers.

As illustrated in FIGS. 3A-C, a lower surface of the wound dressing 300 may be provided with an optional tissue contact layer 350. The tissue contact layer 350 can for example be a polyurethane layer or polyethylene layer or other flexible layer which is perforated, for example via a hot pin process, laser ablation process, ultrasound process or in some other way or otherwise made permeable to liquid and gas. The tissue contact layer 350 has a lower surface and an upper surface. As shown in FIG. 3B, perforations 360 may be provided in the tissue contact layer 350, preferably comprising through holes in the tissue contact layer 350 which enable fluid to flow through the layer 350. The tissue contact layer 350 can help prevent tissue ingrowth into the other material of the wound dressing. Preferably, the perforations 360 are small enough to meet this requirement while still allowing fluid to flow therethrough. For example, perforations 360 formed as slits or holes having a size ranging from approximately 0.025 mm to approximately 1.2 mm, for example 1 mm (or about 1 mm) are considered small enough to help prevent tissue ingrowth into the wound dressing while allowing wound exudate to flow into the dressing. In some configurations, the tissue contact layer 350 may help maintain the integrity of the entire dressing 300 while also creating an air tight seal around the internal layers in order to maintain negative pressure at the wound.

Some embodiments of the tissue contact layer 350 may also act as a carrier for an optional lower and/or upper adhesive layer (not shown). For example, a lower pressure sensitive adhesive may be provided on the lower surface of the tissue contact layer 350 whilst an upper pressure sensitive adhesive layer may be provided on the upper surface of the tissue contact layer 350. In some embodiments a pressure sensitive adhesive, which may be a silicone, hot melt, hydrocolloid or acrylic based adhesive or other such adhesives, may be formed on both sides or optionally on a selected one side of the tissue contact layer. In certain embodiments, the upper adhesive layer may comprise an acrylic pressure sensitive adhesive, and the lower adhesive layer may comprise a silicone pressure sensitive adhesive. In other embodiments the tissue contact layer 350 may not be provided with adhesive. In some embodiments, the tissue contact layer 350 may be transparent or translucent. The film layer of the tissue contact layer 350 may define a perimeter with a rectangular or a square shape. A release layer (not illustrated) may be removably attached to the underside of the tissue contact layer 350, for example covering the lower adhesive layer, and may be peeled off using flaps. Some embodiments of the release layer may have a plurality of flaps extending along the length of the layer. In some embodiments, the tissue contact layer 350 may comprise perforated polyurethane film. The lower surface of the film may be provided with a silicone pressure sensitive adhesive and the upper surface may be provided with an acrylic pressure sensitive adhesive, which may help the dressing maintain its integrity. In some embodiments, a polyurethane film layer may be provided with an adhesive layer on both its upper surface and lower surface, and all three layers (the upper adhesive layer, the film layer, and the lower adhesive layer) may be perforated together.

An optional layer of porous material can be located above the tissue contact layer 350. This porous layer, or transmission layer 320, allows transmission of fluid including liquid and gas away from a wound site into upper layer(s) of the wound dressing 300. In particular, the transmission layer 320 preferably ensures that an open air channel can be maintained to communicate negative pressure over the wound area even when the overlying absorbent layer 310 has absorbed substantial amounts of exudates. The transmission layer 320 should preferably remain open under the typical pressures that will be applied during negative pressure wound therapy as described above, so that the whole wound site sees an equalized negative pressure.

Some embodiments of the transmission layer 320 may be formed of a material having a three dimensional structure. For example, a knitted or woven spacer fabric (for example Baltex 7970 weft knitted polyester) or a non-woven fabric can be used. In some embodiments, the transmission layer 320 can have a 3D polyester spacer fabric layer. This layer can have a top layer which is a 84/144 textured polyester, and a bottom layer which can be a 100 denier flat polyester and a third layer formed sandwiched between these two layers which is a region defined by a knitted polyester viscose, cellulose or the like monofilament fiber. In use, this differential between filament counts in the spaced apart layers tends to draw liquid away from the wound bed and into a central region of the dressing 300 where the absorbent layer 310 helps lock the liquid away or itself wicks the liquid onwards towards the cover layer 345 where it can be transpired. Other materials can be utilized, and examples of such materials are described in U.S. Patent Pub. No. 2011/0282309, which are hereby incorporated by reference and made part of this disclosure.

Some embodiments of the transmission layer 320 may additionally or alternatively comprise a wicking or acquisition distribution material (ADL) to horizontally wick fluid such as wound exudate as it is absorbed upward through the layers of the dressing 300. Lateral wicking of fluid may allow maximum distribution of the fluid through the absorbent layer 330 and may enable the absorbent layer 310 to reach its full holding capacity. This may advantageously increase moisture vapor permeation and efficient delivery of negative pressure to the wound site. Some embodiments of the transmission layer 320 may comprise viscose, polyester, polypropylene, cellulose, or a combination of some or all of these, and the material may be needle-punched. Some embodiments of the transmission layer 320 may comprise polyethylene in the range of 40-150 grams per square meter (gsm).

Further details of example suitable materials for a transmission layer 320 are discussed below with respect to FIGS. 8A-9B.

A layer 310 of absorbent material may be provided above the transmission layer 320. The absorbent material, which can comprise a foam or non-woven natural or synthetic material, and which may optionally comprise a super-absorbent material, forms a reservoir for fluid, particularly liquid, removed from the wound site. In some embodiments, the absorbent layer 310 may also aid in drawing fluids towards the cover layer 345. The absorbent layer 310 can be manufactured from ALLEVYN™ foam, Freudenberg 114-224-4 and/or Chem-Posite™ 11C-450, or any other suitable material. Some embodiments of the absorbent layer can be constructed from hydrophilic foam, for example a hydrophilic polyurethane prepolymer such as HYPOL™. In some embodiments, the absorbent layer 310 can be a layer of non-woven cellulose fibers having super-absorbent material in the form of dry particles dispersed throughout. Use of the cellulose fibers introduces fast wicking elements which help quickly and evenly distribute liquid taken up by the dressing. The juxtaposition of multiple strand-like fibers leads to strong capillary action in the fibrous pad which helps distribute liquid.

For example, some embodiments of the absorbent layer 310 may comprise a layered construction of an upper layer of non-woven cellulose fibers, superabsorbent particles (SAP), and a lower layer of cellulose fibers with 40-80% SAP. In some embodiments, the absorbent layer 310 may be an air-laid material. Heat fusible fibers can optionally be used to assist in holding the structure of the pad together. Some embodiments may combine cellulose fibers and air-laid materials, and may further comprise up to 60% SAP. Some embodiments may comprise 60% SAP and 40% cellulose. Other embodiments of the absorbent layer may comprise between 60% and 90% (or between about 60% and about 90%) cellulose matrix and between 10% and 40% (or between about 10% and about 40%) superabsorbent particles. For example, the absorbent layer 310 may have about 20% superabsorbent material and about 80% cellulose fibers. It will be appreciated that rather than using super-absorbing particles or in addition to such use, super-absorbing fibers can be utilized according to some embodiments of the present invention. An example of a suitable material is the Product Chem-Posite™ 11 C available from Emerging Technologies Inc (ETi) in the USA.

Super-absorber particles/fibers can be, for example, sodium polyacrylate or carbomethoxycellulose materials or the like or any material capable of absorbing many times its own weight in liquid. In some embodiments, the material can absorb more than five times its own weight of 0.9% W/W saline, etc. In some embodiments, the material can absorb more than 15 times its own weight of 0.9% W/W saline, etc. In some embodiments, the material is capable of absorbing more than 20 times its own weight of 0.9% W/W saline, etc. Preferably, the material is capable of absorbing more than 30 times its own weight of 0.9% W/W saline, etc. The absorbent layer 310 can have one or more through holes 355 located so as to underlie the suction port 335.

Further details of example suitable absorbent materials are discussed below with respect to FIGS. 10A-10B.

As illustrated in FIGS. 3A and 3C, the absorbent layer 310 may include a number of through holes 315 and the transmission layer 320 can include an additional number of through holes 325. In some embodiments, the through holes 315 in the absorbent layer 310 and the through holes 325 in the transmission layer 320 can be aligned to form viewing portals 330 through the internal layers of the dressing 300. Due to the transparency or translucency of the cover layer 345 and tissue contact layer 350, the viewing portals 330 can permit viewing of tissue beneath the wound dressing through the wound cover when the wound dressing is applied to a patient, for example for assessment of characteristics of and changes in tissue underlying the dressing 300. In some embodiments, the pattern of the viewing portals 330 can aid a clinician in assessing the progress of healing of a wound underlying the dressing 300 by identifying locations at which new healthy skin has formed. In other embodiments, the pattern of the viewing portals 330 can aid a clinician in assessing the formation and area of a wound forming under the dressing 300, such as a diabetic ulcer or a pressure ulcer. In some embodiments, through holes 325 in the transmission layer 320 may be approximately 2 mm in diameter and may be aligned with smaller holes or perforations in the tissue contact layer 350. As discussed above, perforations 360 may be formed in the tissue contact layer, and may be approximately 1 mm in diameter in some embodiments.

In some embodiments, some or all of through holes 315, 325 may comprise (that is, be plugged or filled using) a plug material, for example a soft, transparent and optionally hydrophobic material (e.g. silicone). Positioning such plug material within through holes 315, 325 can beneficially reduce the risk of underlying skin or tissue being sucked into voids in the dressing when the dressing is under negative pressure. Accordingly, in some examples the through holes 325 that are closest to the wound site may be filled with plug material while the through holes 315 further from the wound site may not be filled. Alternatively, the through holes 315 further from the wound site may be filled, and the through holes 325 closer to the wound site may not be filled with plug material. The plug material can additionally provide the benefit of preventing lateral swelling of super absorbent particles in the absorbent layer 310, which can cause the particles to spill out of the absorbent layer 310 material at the cut edges, thereby filling (at least partially) the through holes 315, 325. Accordingly, in some examples at least the through holes 315 in the absorbent layer may be filled with plug material. In one embodiment, an absorbent layer and an underlying transmission layer can have through holes that are aligned or substantially aligned, such that there is some visibility to the underlying patient tissue. The through holes in the absorbent layer can be filled with plug material, while the through holes in the transmission layer positioned between the absorbent layer and the wound site are not filled with plug material. Such a configuration can provide for better transmission of negative pressure to tissue underlying the plugged through holes compared to embodiments which provide plug material in a material layer positioned adjacent to the wound site.

The transparency of the plug material provides visibility through to the wound bed. As a result of the hydrophobic nature of some embodiments of the plug material, the viewing portals 330 will remain transparent throughout wear time as colored wound exudate and other substances should not be drawn into the plug material because it is hydrophobic. Some examples of the plug material are not absorbent so as to not fill with exudate. In some embodiments, larger through holes can be provided in dressing embodiments using the plug material within through holes compared to dressing embodiments without plug material, for example due to removal of size constraints for preventing patient tissue from being drawn into the holes. In some embodiments, when plugs are provided in through holes 315 of the absorbent layer 310 and optionally in the through holes 325 of the transmission layer 310, the through holes 325 of the transmission layer 320 may be the same shape and dimension as the through holes 315. In other embodiments, when plugs are provided in through holes 315 of the absorbent layer 310, no transmission layer 310 is provided.

The through holes 315 in the absorbent layer 310 may form a repeating pattern across the area of the absorbent layer 310 with the exception of the area of the absorbent layer 310 including the through hole 355 for the port 335. Here the repeating pattern is illustrated as a grid or array of through holes 315 though in other embodiments other patterns can be used. In some embodiments, the through holes 315 in the absorbent layer 310 and the through holes 325 in the transmission layer 320 may be spaced apart by 10 mm (or about 10 mm) or less. The through hole 355 underlying the port 335 is illustrated as being separate from the repeating pattern of through holes 315 and larger than the through holes 315, however in some embodiments the repeating pattern of through holes 315 can continue across the entire area (or substantially all of the area) of the absorbent layer 310 and the port can be placed over a selected one of the through holes in the array, or over a selected group of adjacent through holes in the array. In the illustrated embodiment, the transmission layer 320 has no through holes underlying the through hole 355 in the absorbent layer 310 over which the port 335 is applied. However, in other embodiments the pattern of through holes 325 in the transmission layer 320 may continue under the through hole 355 in the absorbent layer 310.

The through holes 315, 325 can be cut or formed in some embodiments by punching, die cutting, or laser cutting the sheet materials used to form the absorbent layer 310 and the transmission layer 320. However, the creation of apertures, for example by hole-punching, has the disadvantages of resulting in the generation of waste and also the mechanical weakening of the material. By forming through slits in a material, these slits being capable of expanding to form apertures on extension of the material, increased visibility of the wound can be achieved without significant material waste. In this manner, it is also possible to achieve extension of the slit to form a circular hole without mechanically weakening the material. Examples of such lattice cutting techniques are disclosed in International Patent Publication No. PCT/US2007/079529, filed Sep. 26, 2007, titled "LATTICE DRESSING," the entirety of which is hereby incorporated by reference. In some embodiments, for example embodiments in which the through holes 315 in the absorbent layer 310 and the through holes 325 transmission layer 325 are different sizes or are arranged in different patterns, the absorbent layer 310 and transmission layer 325 can be cut separately from one another by any of the previously described hole-forming processes. In some embodiments, the absorbent layer 310 and transmission layer 320 can be stacked and the through holes 315, 325 cut through the stacked layers 310, 325 at the same time by any of the previously described hole-forming processes. In some embodiments separate plug material portions can be provided to the through holes in various layers (here, absorbent layer 310 and transmission layer 320), for example as the holes are punched or cut in the layer. In some embodiments, the layers may be stacked and hole punched or cut together and accordingly a single portion of plug material can be provided extending through the holes 315, 325 of multiple layers.

Although the through holes 315 in the absorbent layer 310 and the through holes 325 in the transmission layer 320 are depicted as being centered and aligned one-to-one, other alignments can be used in other embodiments. For example, multiple smaller through holes 325 in the transmission layer 320 can be aligned with larger through hole 315 in the absorbent layer 310. Further, although the through holes 315 in the absorbent layer 310 are depicted as being larger than the through holes 325 in the transmission layer 320, in other embodiments the through holes 315, 325 may be substantially equal sizes or the through holes 325 in the transmission layer may be larger than the through holes 315 in the absorbent layer 310. In some embodiments, non-woven materials may require relatively larger holes (for example approximately 2 mm or larger) than woven materials in order for the holes to remain open under negative pressure. Depending on the amount of negative pressure applied to the dressing 300, the through holes in the layer closest to the patient tissue may be limited to a maximum diameter in order to prevent the formation of suction blisters by tissue pulled into the through holes. In some embodiments, the through holes 325 in the transmission layer 320 may have a diameter of approximately 1 mm or less to prevent the underlying tissue from being pulled into the through holes 325 when negative pressure is applied to the dressing 300, thereby preventing damage to the tissue and/or discomfort to the patient. In other embodiments, the through holes 325 may have a diameter of approximately 10 mm or less. The through holes 315 in the absorbent layer 310 can have a diameter of approximately 2 mm to approximately 10 mm in some embodiments. Although through holes 315, 325 are illustrated as being generally circular in shape, this is for purposes of illustration and other shapes can be used for through holes 315, 325 in other embodiments such as elliptical, square, rectangular, triangular, and hexagonal, to name a few.

In some embodiments, the through holes in one or both of the absorbent layer and transmission layer 320 may be susceptible to closing under negative pressure. Adhesive can be applied to the upper surface of the tissue contact layer 350 in some embodiments, and by contacting the transmission layer 320 such adhesive can assist in maintaining the openness of the through holes 325 in the transmission layer 320. Similarly, adhesive can be applied to the lower surface of the cover layer 345 in some embodiments, and by contacting the absorbent layer 310 such adhesive can assist in maintaining the openness of the through holes 315 in the absorbent layer 310. Adhesive can be applied between the absorbent layer 310 and the transmission layer 320 in some embodiments to assist in maintaining the openness of through holes 315, 325 in both layers. For example, in some embodiments the adhesive layer between the absorbent layer 310 and the transmission layer 320 may comprise an adhesive web or net. In other embodiments, the adhesive layer may comprise adhesive tape. Yet other embodiments may employ a hot melt adhesive a hot melt adhesive such as ethylene vinyl acetate (EVA). For example, EVA powder may be sprinkled over one or both of the layers 310, 320, which may then be heat bonded. Preferred embodiments of the adhesive layer are hydrophilic so as not to affect the transport of water and/or water-based solutions between the absorbent layer 310 and the transmission layer 320.

The absorbent layer 310 may be of a greater area than the transmission layer 320 in some embodiments, such that the absorbent layer 310 overlaps two or more edges of the transmission layer 320, thereby ensuring that the transmission layer does not contact the cover layer 345. This can provide an outer channel of the absorbent layer that is in direct contact with the tissue contact layer 350 that aids more rapid absorption of exudates to the absorbent layer. Furthermore, such an outer channel can ensure that no liquid is able to pool around the circumference of the wound cavity, which may otherwise seep through the seal around the perimeter of the dressing leading to the formation of leaks.

Figure 11:
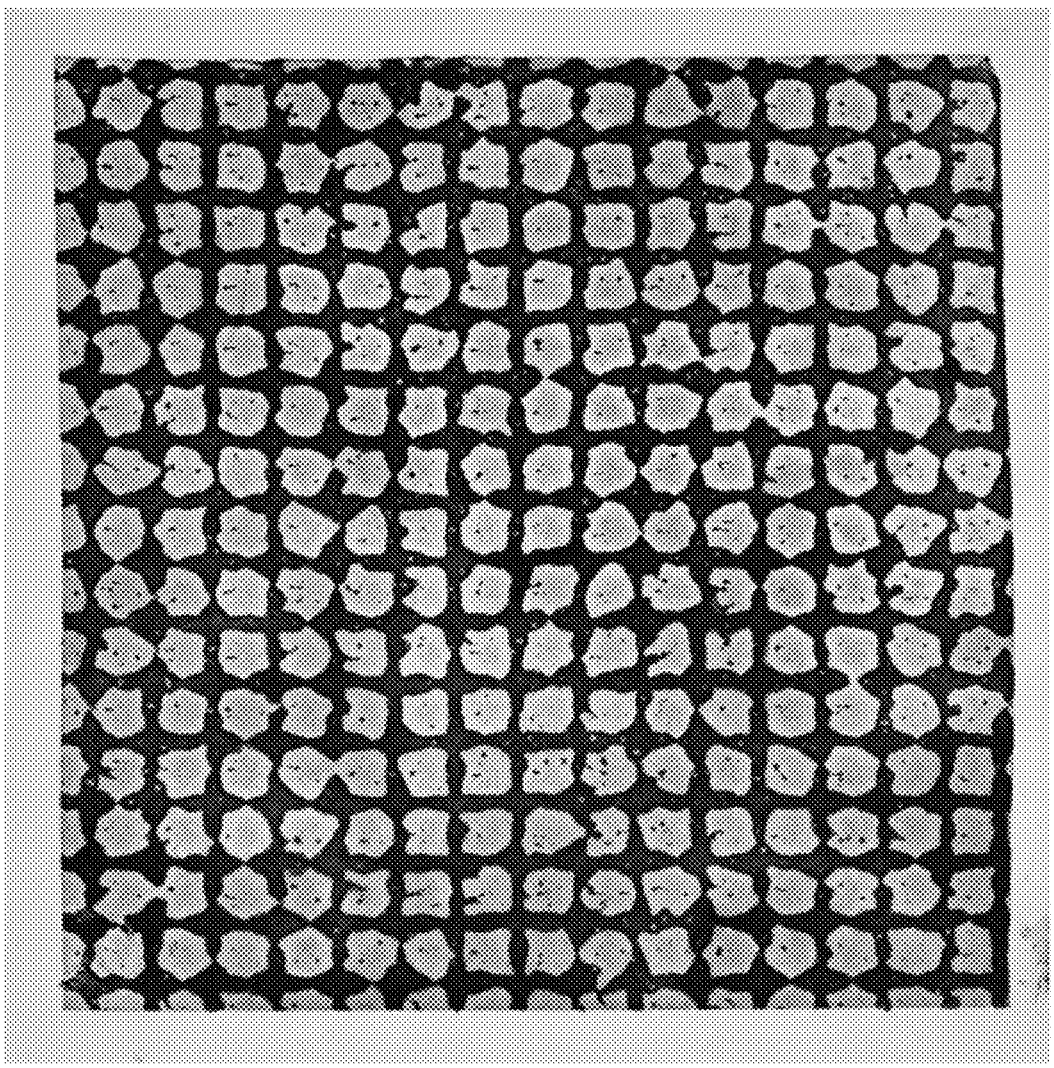
FIG. 11 illustrates one embodiment of an adhesive spread on cover layer material.

The cover layer 345 is preferably gas impermeable, but moisture vapor permeable, and can extend across the width of the wound dressing 300. The cover layer 345, which may for example be a polyurethane film having a pressure sensitive adhesive on one side, is impermeable to gas and this layer thus operates to cover the wound and to seal a wound cavity over which the wound dressing is placed. In this way an effective chamber is made between the cover layer 345 and a wound site where a negative pressure can be established. The cover layer 345 is preferably sealed to the tissue contact layer 350 in a border region 305 around the circumference of the dressing, ensuring that no air is drawn in through the border area, for example via adhesive or welding techniques. The cover layer 345 protects the wound or underlying tissue from external bacterial contamination (bacterial barrier) and allows liquid from wound exudates to be transferred through the layer and evaporated from the film outer surface. The cover layer 345 preferably comprises two layers; a polyurethane film and an adhesive pattern spread onto the film. Some embodiments may employ a polyurethane film (for example, Elastollan SP9109) or any other suitable material. For example, certain embodiments may comprise translucent or transparent 30 gsm EU33 film. An example of a cover contact layer adhesive spread is illustrated in FIG. 11 and discussed in more detail below. The polyurethane film is preferably moisture vapor permeable and may be manufactured from a material that has an increased water transmission rate when wet.

An orifice 365 is preferably provided in the cover layer 345 to allow a negative pressure to be applied to the dressing 300. A suction port 335 is preferably attached or sealed to the top of the cover layer 345 over the orifice 365 made or formed into the cover layer 345 to communicate negative pressure through the orifice 365. A length of tubing 340 may be coupled at a first end to the suction port 335 and at a second end to a pump unit (not shown) to allow transmission of negative pressure to the dressing 300 and, in some embodiments, to allow fluids to be pumped out of the dressing 300. The port 335 may be adhered and sealed to the cover layer 345 using an adhesive such as an acrylic, cyanoacrylate, epoxy, UV curable or hot melt adhesive. The illustrated embodiment of the port 335 can be formed from a soft polymer, for example a polyethylene, a polyvinyl chloride, a silicone or polyurethane having a hardness of 30 to 90 on the Shore A scale. However, the illustrated port 335 is intended to provide one example of a port suitable for use with the wound dressing 300 and not to limit the type of port usable with the dressing 300. In some embodiments, the port 335 may be made from a soft or conformable material, for example using the embodiments described in International Patent Application No. PCT/M2013/001469, filed May 22, 2013, titled "APPARATUSES AND METHODS FOR NEGATIVE PRESSURE WOUND THERAPY," the entirety of which is hereby incorporated by reference.

Preferably the absorbent layer 310 includes at least one through hole 355 located so as to underlie the port 335. The through hole 355, while illustrated here as being larger than the hole through the cover layer 345, may in some embodiments be bigger or smaller than the hole 365 in cover layer 345. It will be appreciated that multiple openings could alternatively be utilized. Additionally should more than one port be utilized according to certain embodiments of the present disclosure one or multiple openings may be made in the absorbent layer 310 and the cover layer 345 in registration with each respective port. Although not essential to certain embodiments of the present disclosure the use of through holes in a super-absorbent material forming the absorbent layer 320 may provide a fluid flow pathway which remains unblocked in particular when the absorbent layer 310 is near saturation.

Accordingly, the port 335 is in direct fluid communication with the transmission layer 320 through orifice 365 and through hole 355. This allows the negative pressure applied to the port 335 to be communicated to the transmission layer 320 without passing through the absorbent layer 310, ensuring that the negative pressure applied to the wound site is not inhibited by the absorbent layer 310 as it absorbs wound exudates. In use, for example when negative pressure is applied to the dressing 300, a wound facing portion of the port 335 may thus come into contact with the transmission layer 320, which can thus aid in transmitting negative pressure to the wound site even when the absorbent layer 310 is filled with wound fluids. Some embodiments may have the cover layer 345 be at least partly adhered to the transmission layer 320. In some embodiments, the aperture 355 in the absorbent layer 310 is at least 1-2 mm larger than the diameter of the wound facing portion of the port 335. In other embodiments the aperture 355 in the absorbent layer 310 is smaller than the diameter of the wound facing portion of the port 335. In other embodiments, no aperture may be provided in the absorbent layer 310, or alternatively a plurality of apertures underlying the orifice 365 may be provided.

A filter element that is impermeable to liquids, but permeable to gases can be provided in or below the port 335 to act as a liquid barrier between the dressing 300 and the conduit 340 in some embodiments to ensure that no liquids are able to escape from the wound dressing 300. The filter element may also function as a bacterial barrier. The pore size can be approximately 0.2 µm. Suitable materials for the filter material of the filter element include 0.2 micron Gore™ expanded PTFE from the MMT range, PALL Versapore™ 200R, and Donaldson™ TX6628. Larger pore sizes can also be used but these may require a secondary filter layer to ensure full bioburden containment. As wound fluid contains lipids it is preferable, though not essential, to use an oleophobic filter membrane for example 1.0 micron MMT-332 prior to 0.2 micron MMT-323. This prevents the lipids from blocking the hydrophobic filter. The filter element can be attached or sealed to the port 335 and/or the cover layer 345 over the orifice 365. For example, the filter element may be molded into the port 335, or may be adhered to both the top of the cover layer 345 and bottom of the port 335 using an adhesive such as, but not limited to, a UV cured adhesive.

In particular for embodiments with a single port 335, it may be preferable for the port 335 to be located in an off-center position as illustrated in FIGS. 3A-C and in FIG. 1. Such a location may permit the dressing 300 to be positioned onto a patient such that the port 335 is raised in relation to the remainder of the dressing 2100. So positioned, the port 335 may be less likely to come into contact with wound fluids that could prematurely occlude the port 335 so as to impair the transmission of negative pressure to the wound site.

Some embodiments may be manufactured without the port 335 and may include at least one area for attaching a port. For example, the port may simply be an opening in the cover layer 345 for attaching a separate port member, and the opening may be preformed in the cover layer 345 or formed by a clinician by cutting, puncturing, or tearing the cover layer 345.

In some embodiments, the tissue contact layer 350 may be flat and the cover layer 345 may be contoured over the inner layers of the dressing 300. The absorbent layer 310 may be about 1.5 times thicker than the transmission layer 320 in some embodiments.

Figure 4A:
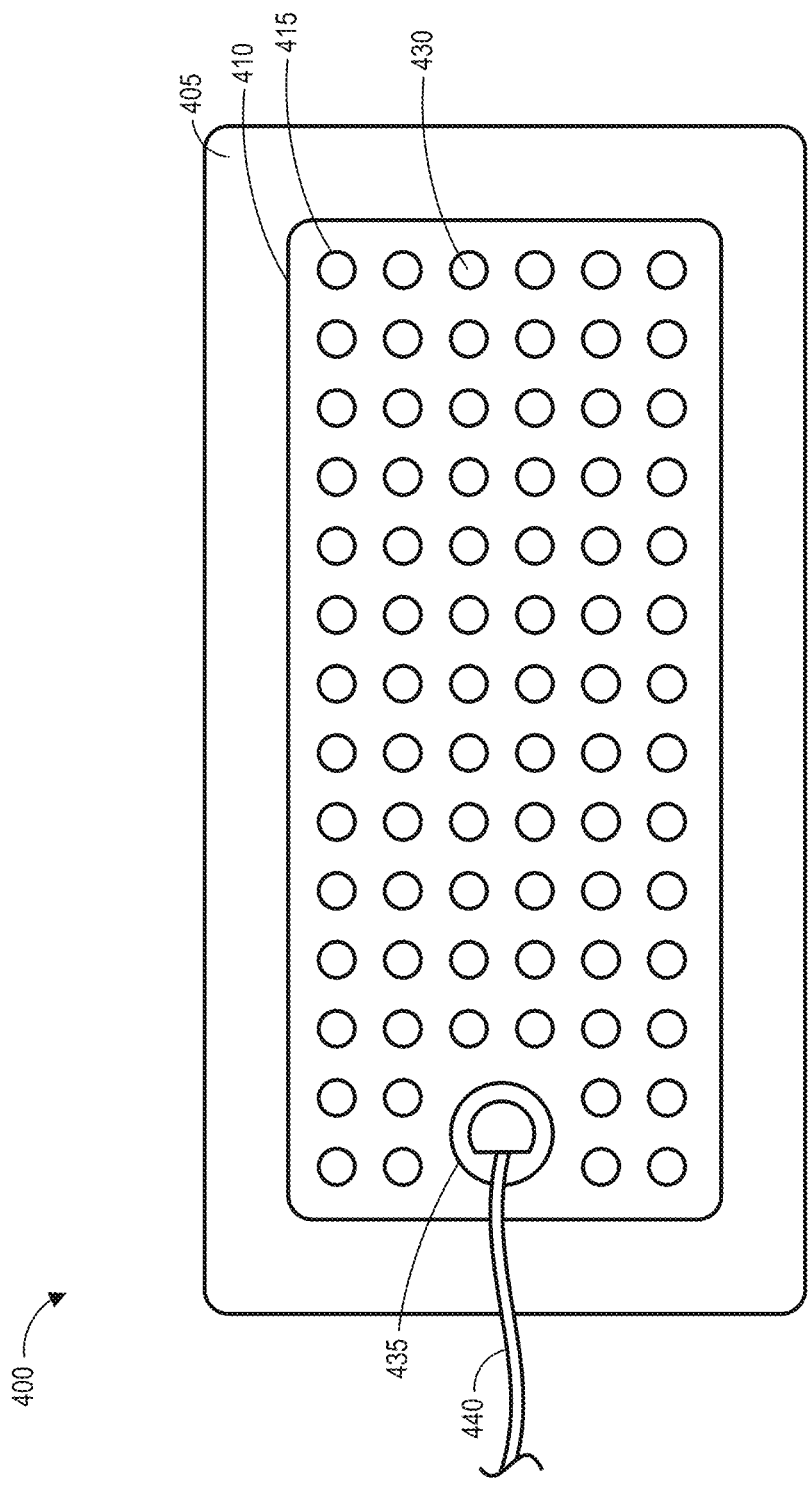
FIGS. 4A-4C illustrate another embodiment of a wound dressing configured for enhanced tissue visibility.
Figure 4B:
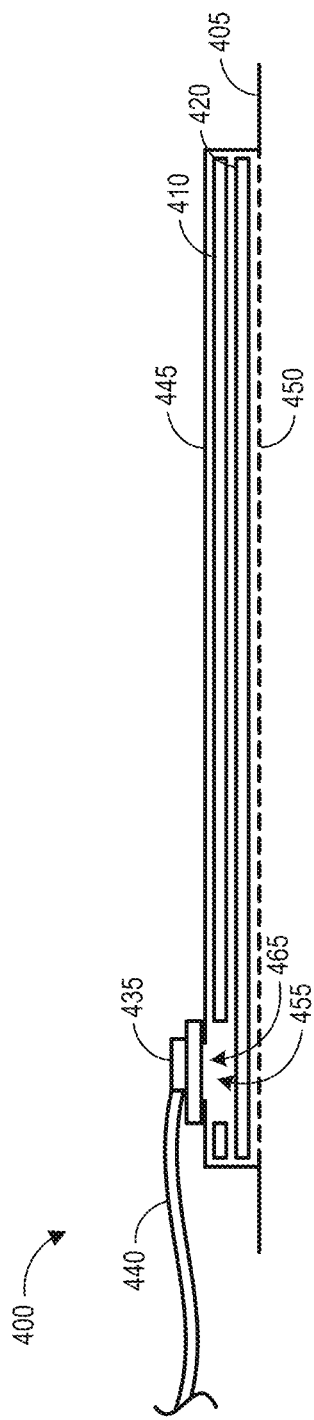
Figure 4C:
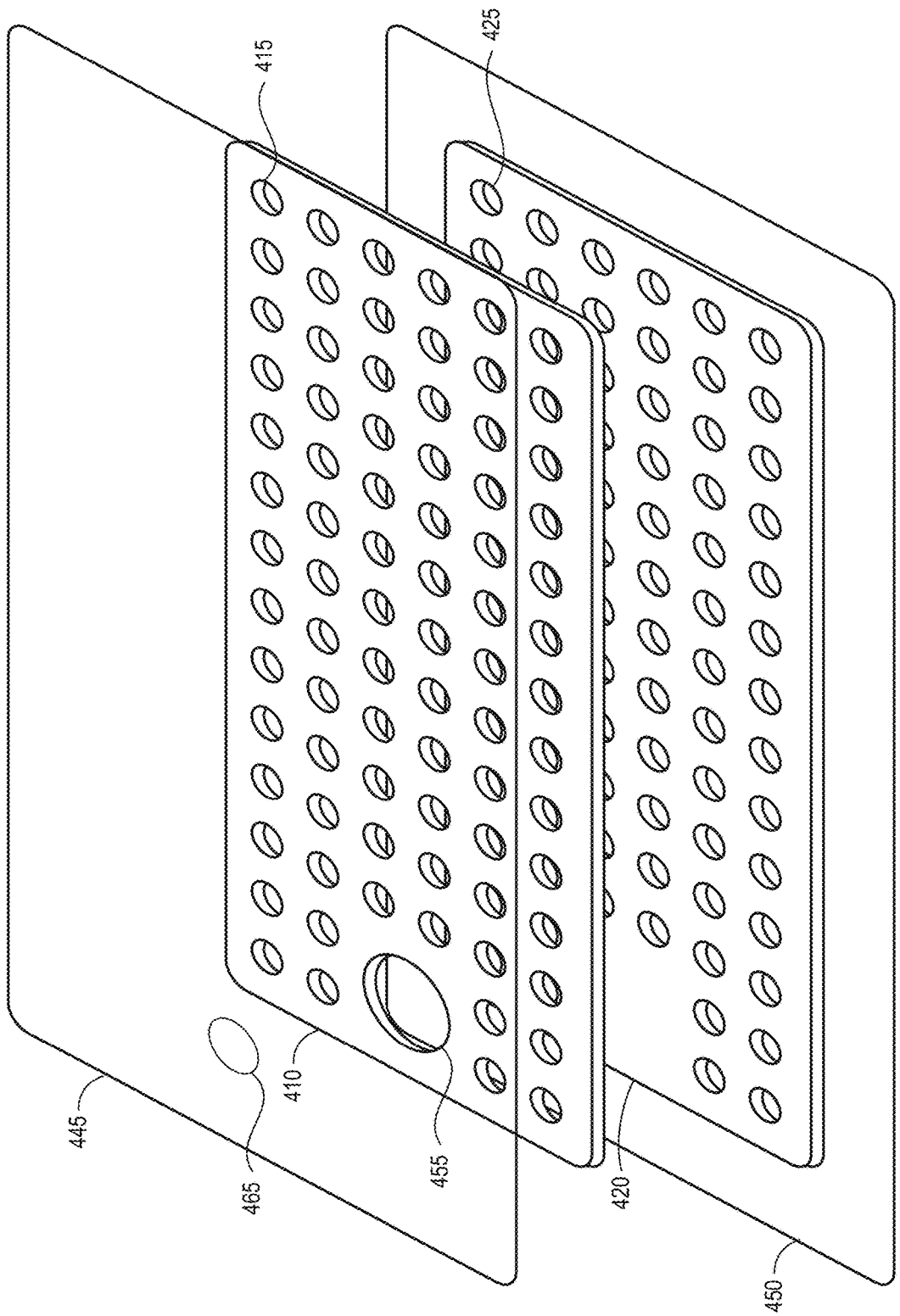

FIGS. 4A-4C illustrate another embodiment of a wound dressing 400 configured for enhanced tissue visibility. FIG. 4A illustrates a top view of the wound dressing 400, FIG. 4B illustrates a cross-sectional view of the wound dressing 400, and FIG. 4C illustrates an exploded view of various layers of the wound dressing 400. The wound dressing 400 can be located over a wound site or potentially wound-forming tissue site to be treated as described above. In some embodiments, the dressing 400 comprises a cover layer 445 attached to a tissue contact layer 450, for example any of the cover layer or tissue contact layer embodiments described above or below. These two layers 445, 450 can be joined or sealed together around a perimeter 405 so as to define an interior space or chamber in which therapeutic negative pressure can exist. This interior space or chamber may include absorbent layer 410 and transmission layer 420, which can be any of the absorbent materials or transmission materials described above or below. A port 435 and conduit 440 can be attached to the dressing 400 overlying an orifice 465 in the cover layer 445 and a through hole 455 in the absorbent layer 410 as described above with respect to FIGS. 3A-3C for transmission of negative pressure from a pump to the dressing 400.

The absorbent layer 410 includes a number of through holes 415 arranged in a repeating pattern. The transmission layer 320 includes an additional number of through holes 425 of substantially the same size as the through holes 415 in the absorbent layer 410 and arranged in a similar repeating pattern. In some embodiments, the through holes 415 in the absorbent layer 410 and the through holes 425 in the transmission layer 420 can be aligned or substantially aligned to form viewing portals 430 through the internal layers of the dressing 400. As described above, some or all of the through holes 415, 425 may comprise a plug material. As described above, due to the transparency or translucency of the cover layer 445 and tissue contact layer 450, the viewing portals 430 can permit viewing of tissue beneath the wound dressing through the wound cover when the wound dressing is applied to a patient, for example enabling a clinician to assess characteristics of and changes in tissue underlying the dressing 400. In the illustrated embodiment, the transmission layer 420 has no through holes underlying the through hole 455 in the absorbent layer 410 over which the port 435 is applied. However, in other embodiments the pattern of through holes 425 in the transmission layer 420 may continue under the through hole 455 in the absorbent layer 410.

Figure 5A:
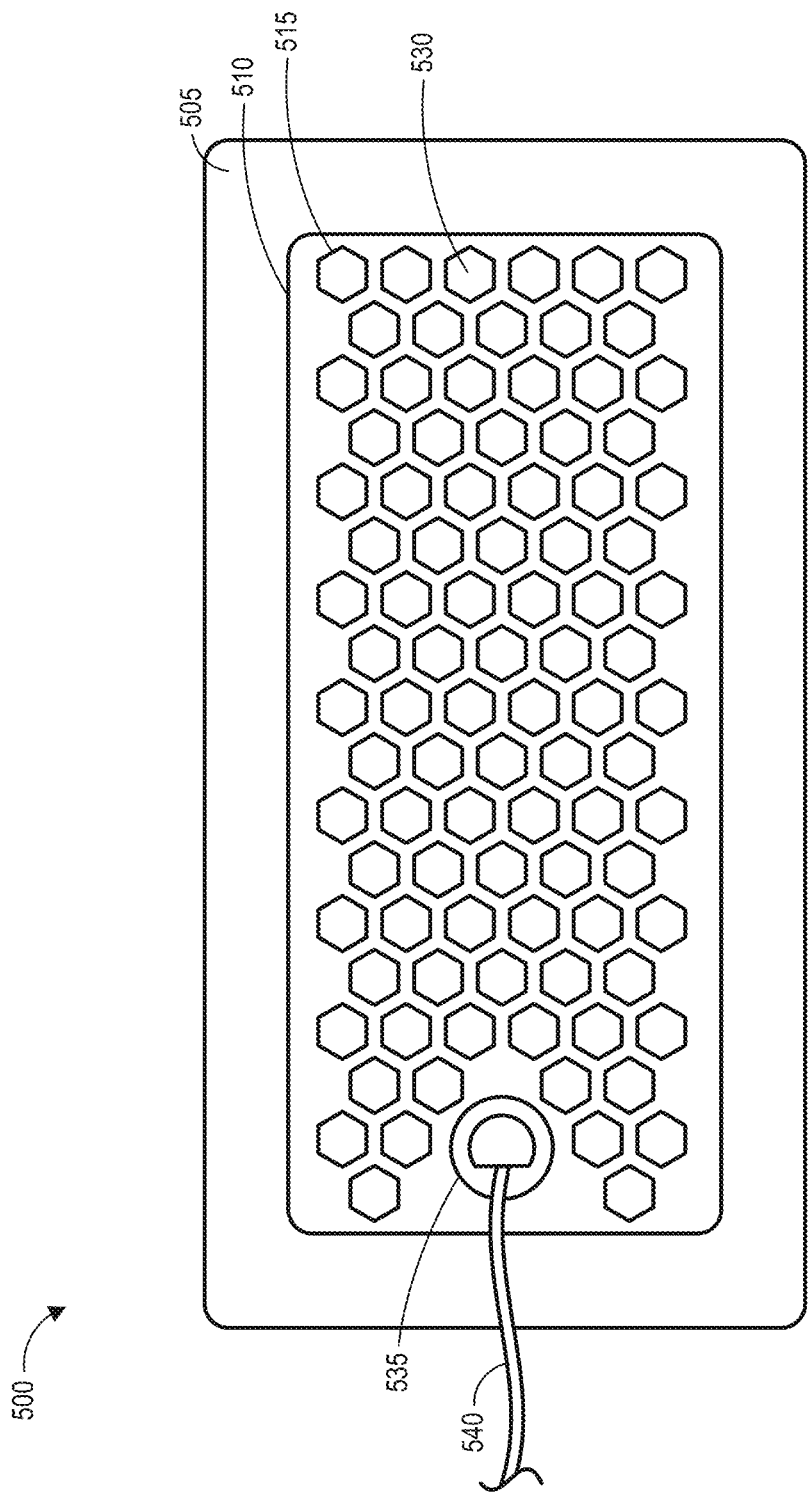
FIGS. 5A-5C illustrate another embodiment of a wound dressing configured for enhanced tissue visibility.
Figure 5B:
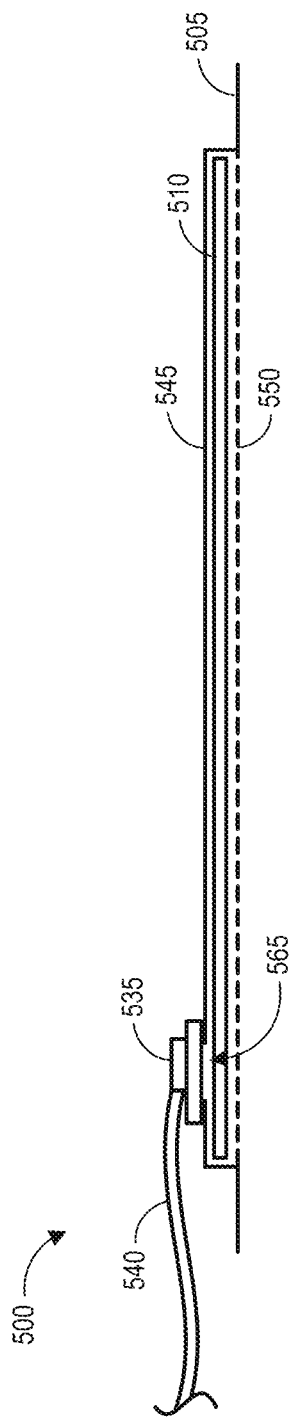
Figure 5C:
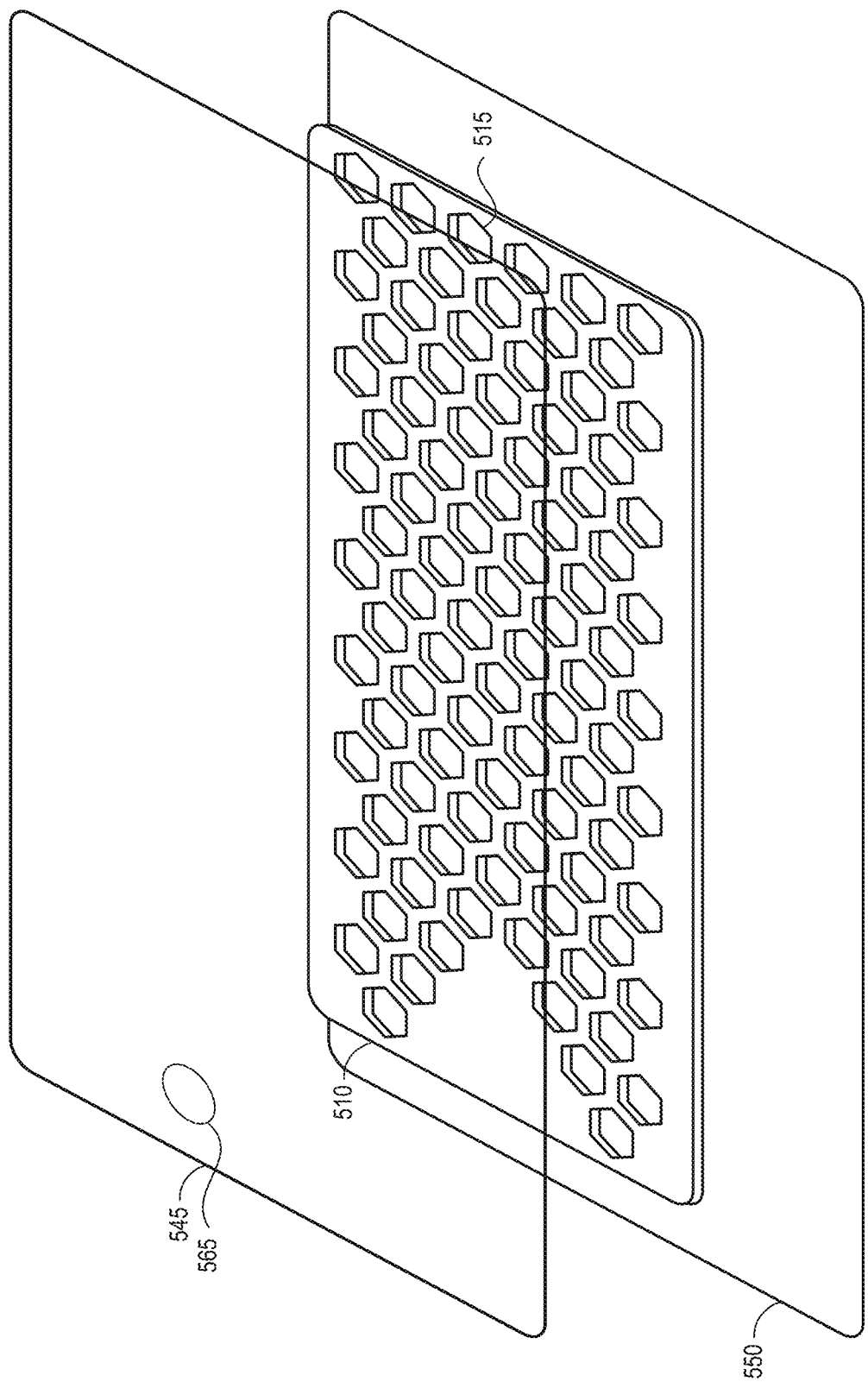

FIGS. 5A-5C illustrate another embodiment of a wound dressing 500 configured for enhanced tissue visibility. FIG. 5A illustrates a top view of the wound dressing 500, FIG. 5B illustrates a cross-sectional view of the wound dressing 500, and FIG. 5C illustrates an exploded view of various layers of the wound dressing 500. The wound dressing 500 can be located over a wound site or potentially wound-forming tissue site to be treated as described above. In some embodiments, the dressing 500 comprises a cover layer 545 attached to a tissue contact layer 550, for example any of the cover layer or tissue contact layer embodiments described above or below. These two layers 545, 550 can be joined or sealed together around a perimeter 505 so as to define an interior space or chamber in which therapeutic negative pressure can exist. This interior space or chamber may include a single material layer 510, which can be any of the absorbent materials or transmission materials described above or below. A port 535 and conduit 540 can be attached to the dressing 500 overlying the material layer 510 as described above with respect to FIGS. 3A-3C for transmission of negative pressure from a pump to the dressing 500.

The material layer 510 can include a number of through holes 515 forming viewing portals 530 through the dressing. As described above, some or all of the through holes 515 may comprise a plug material. As described above, due to the transparency or translucency of the cover layer 545 and tissue contact layer 550, the viewing portals 530 can permit viewing of tissue beneath the wound dressing through the wound cover when the wound dressing is applied to a patient, for example enabling a clinician to assess characteristics of and changes in tissue underlying the dressing 500. The through holes 515 can be arranged in a repeating pattern, here illustrated as hexagonal through holes 515 forming a honeycomb pattern, across substantially all of the area of the material layer 510. The pattern can be discontinued in some embodiments in an area underlying the port 535 so that the underlying tissue contact layer 550 does not come into contact with and occlude the port 535 when negative pressure is applied to the dressing 500.

Figure 6A:
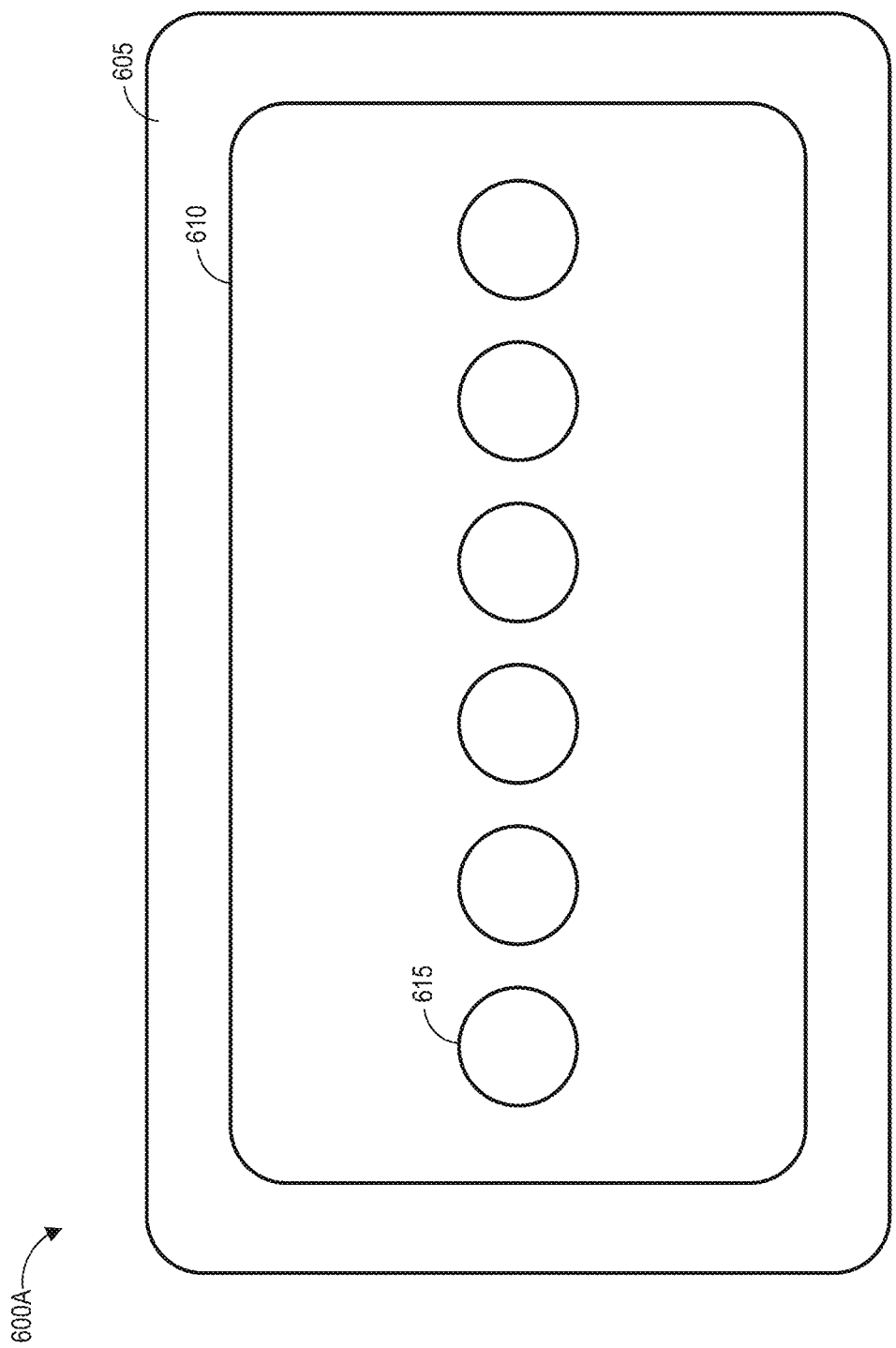
FIGS. 6A-6C illustrate various embodiments of a wound dressing configured for enhanced tissue visibility.
Figure 6B:
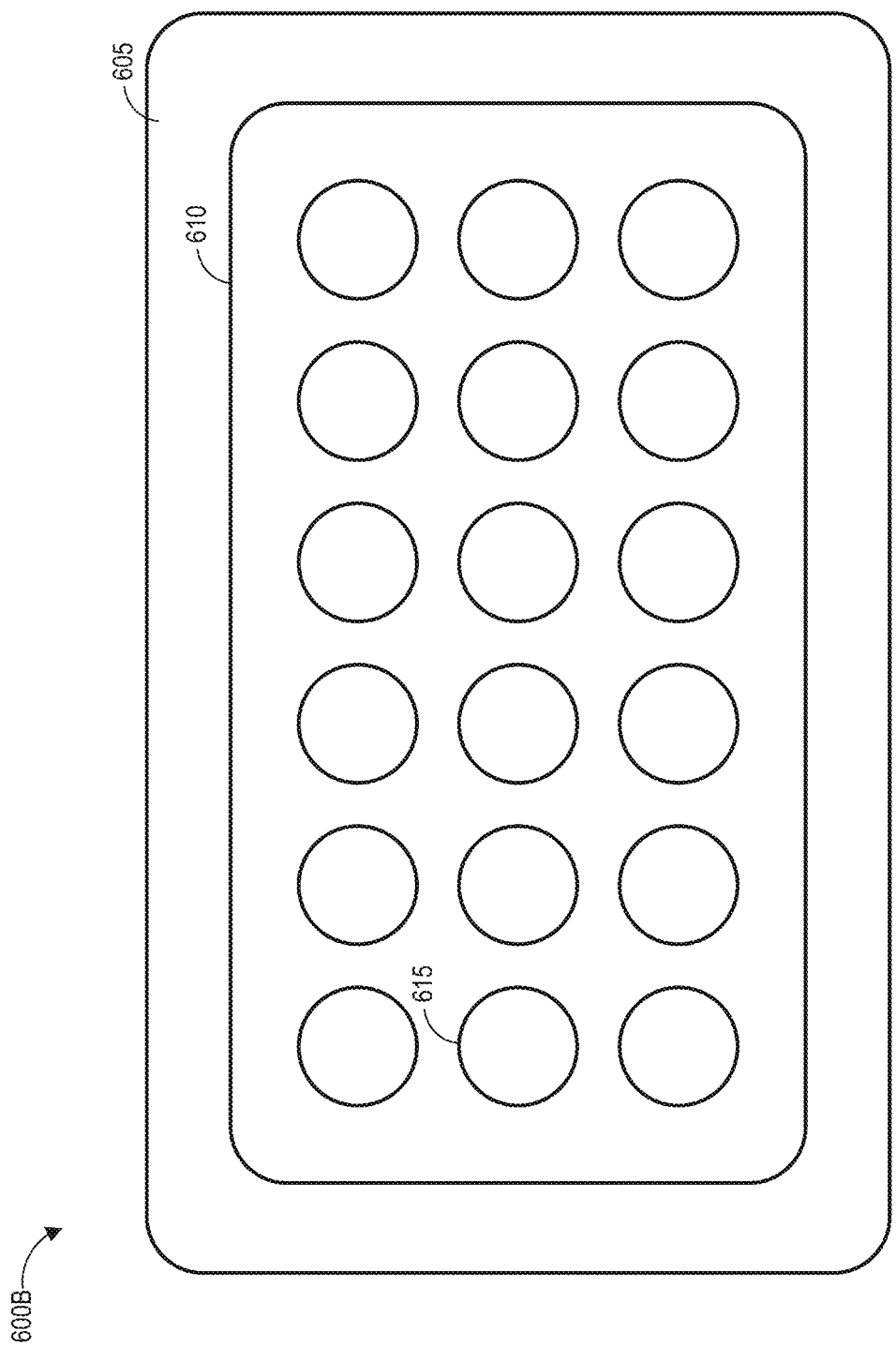
Figure 6C:
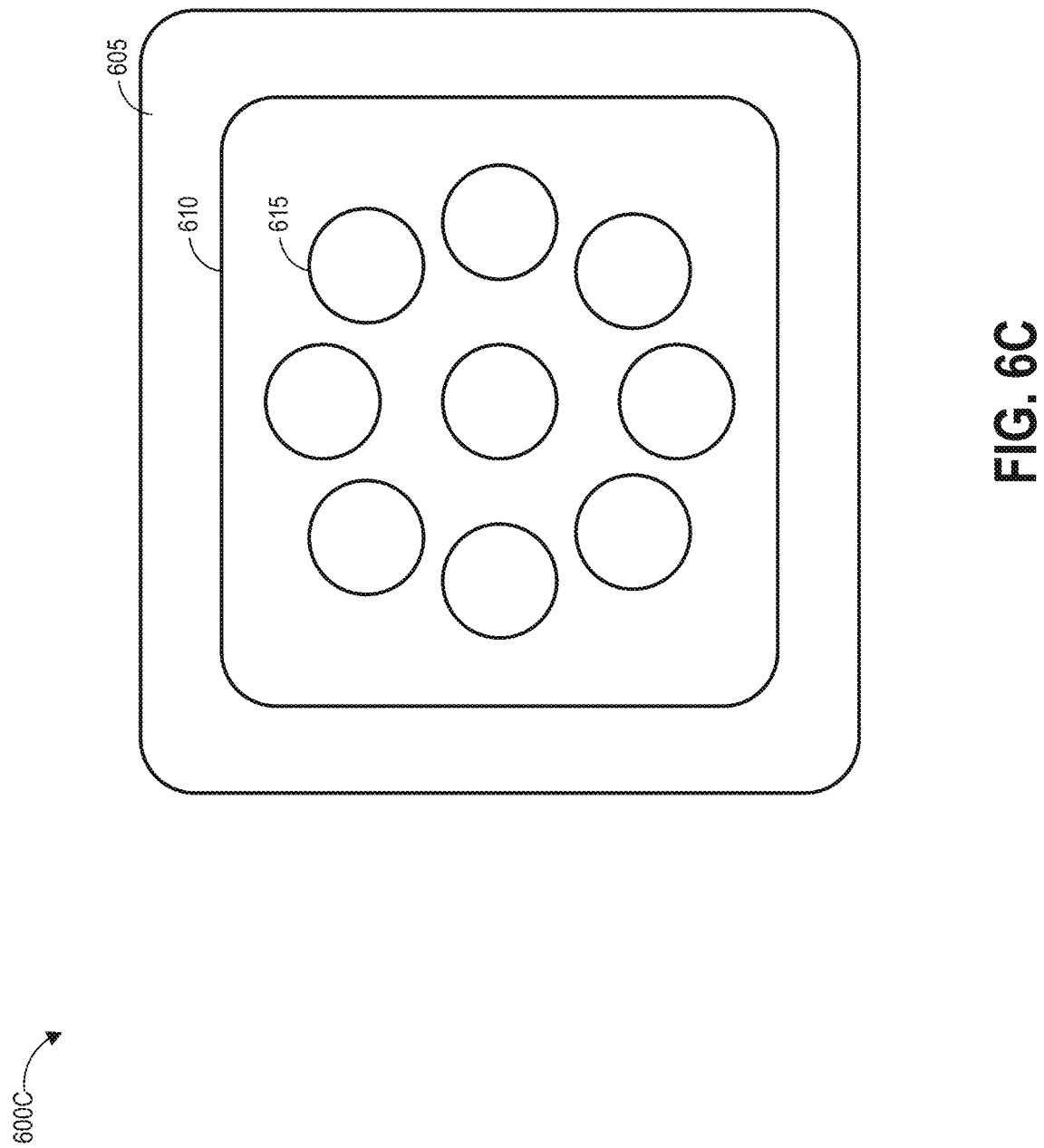

FIGS. 6A-6C illustrate various embodiments of a wound dressing configured for enhanced tissue visibility. FIG. 6A illustrates a top view of the wound dressing 600A showing the perimeter 605 of a cover layer and tissue contact layer, a material layer 610 below the cover layer, and a pattern of through holes 615 in the material layer. The through holes 615 are illustrated in FIG. 6A as being a single line of six substantially equally sized holes. FIG. 6B illustrates a top view of another embodiment of the wound dressing 600B showing the perimeter 605 of a cover layer and backing layer, the material layer 610 below the cover layer, and a second embodiment of the pattern of through holes 615 in the material layer. The through holes 615 are illustrated in FIG. 6B as being three rows of six substantially equally sized holes. FIG. 6C illustrates a top view of another embodiment of the wound dressing 600C showing the perimeter 605 of a cover layer and backing layer, a material layer 610 below the cover layer, and a pattern of through holes 615 in the material layer. The through holes 615 are illustrated in FIG. 6C as being a circle of substantially equally sized holes positioned around a center hole.

In some embodiments, a port can be placed over any of the holes in the patterns illustrated in FIGS. 6A-6C. Though not illustrated, through holes in a layer underneath the illustrated material layer 610 may be smaller than the through holes 615 in the material layer 610. Viewing portals can be formed through the dressing by aligning at least a portion of one or more holes in a lower layer with one of the through holes 615 in the material layer 610. As described above, some or all of the through holes 615 may comprise a plug material.

Figure 7:
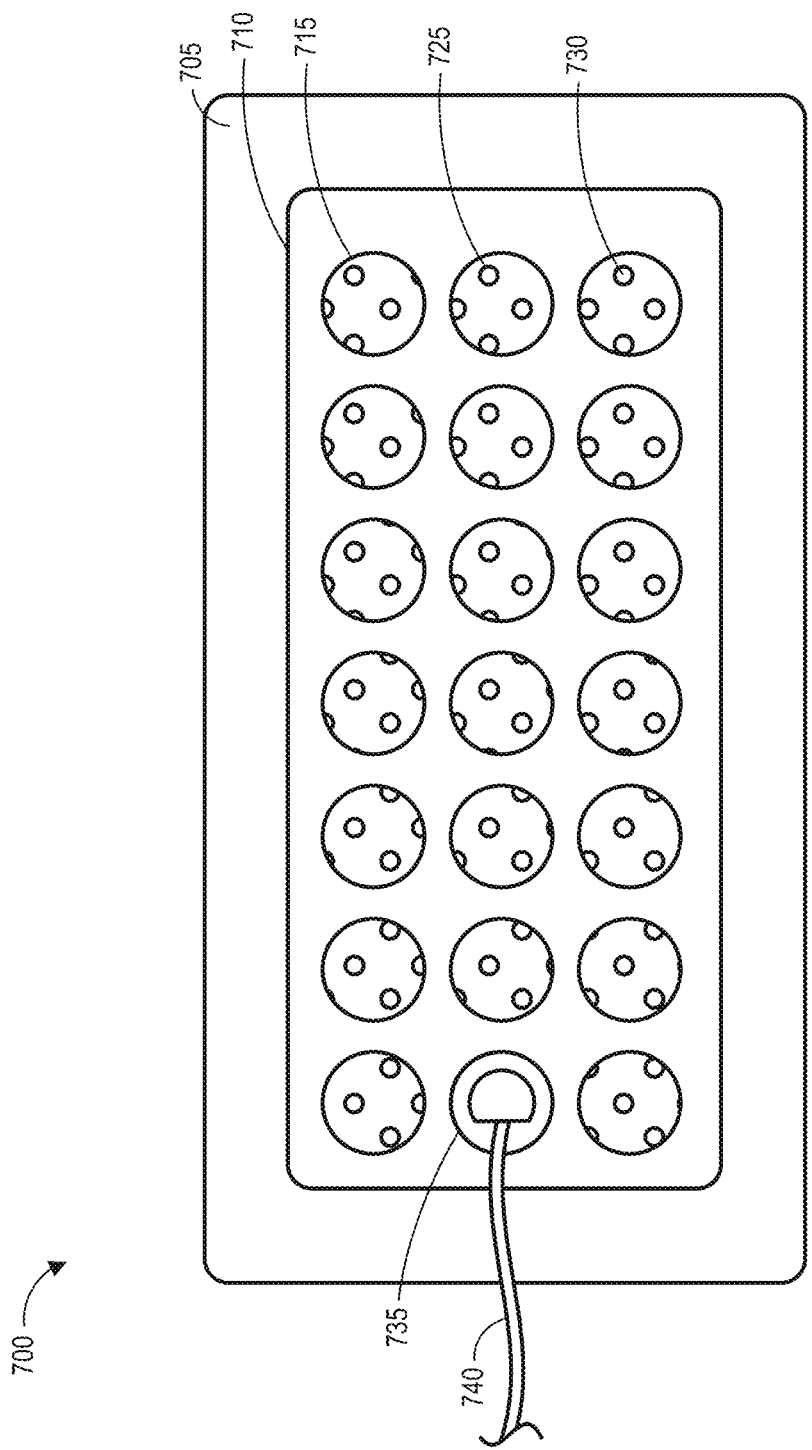
FIG. 7 illustrates another embodiment of a wound dressing configured for enhanced tissue visibility.

FIG. 7 illustrates a top view of another embodiment of a wound dressing 700 configured for enhanced tissue visibility. The wound dressing 700 can be located over a wound site or potentially wound-forming tissue site to be treated as described above. In some embodiments, the dressing 700 comprises a cover layer attached to a tissue contact layer, for example any of the cover layer or tissue contact layer embodiments described above or below, joined or sealed together around a perimeter 705 so as to define an interior space or chamber in which therapeutic negative pressure can exist. This interior space or chamber may include an absorbent layer 710 and a transmission layer positioned beneath the absorbent layer, which can be any of the absorbent materials or transmission materials described above or below. A port 735 and conduit 740 can be attached to the dressing 700 overlying one of the through holes 715 in the absorbent layer 710 for transmission of negative pressure from a pump to the dressing 700.

The absorbent layer 710 includes a number of through holes 715 arranged in a pattern including three rows of seven substantially equally sized holes 715. The transmission layer includes an additional number of through holes 725 of a substantially smaller size than the through holes 715 in the absorbent layer 710. The through holes 725 in the transmission layer are arranged in a repeating pattern. When the transmission layer and absorbent layer 710 are aligned under the cover layer, multiple through holes 725 in the transmission layer can be visible through each of the through holes 715 in the absorbent layer 710 to form viewing portals 730 through the dressing to the underlying tissue. As described above, due to the transparency or translucency of the cover layer and tissue contact layer, the viewing portals 730 can permit viewing of tissue beneath the wound dressing through the wound cover when the wound dressing is applied to a patient, for example enabling a clinician to assess characteristics of and changes in tissue underlying the dressing 700. The repeating pattern of holes 725 in the transmission layer may or may not extend under the port 735 in various embodiments. As described above, some or all of the through holes 725 may comprise a plug material.

III. Example Materials

Figure 8A:
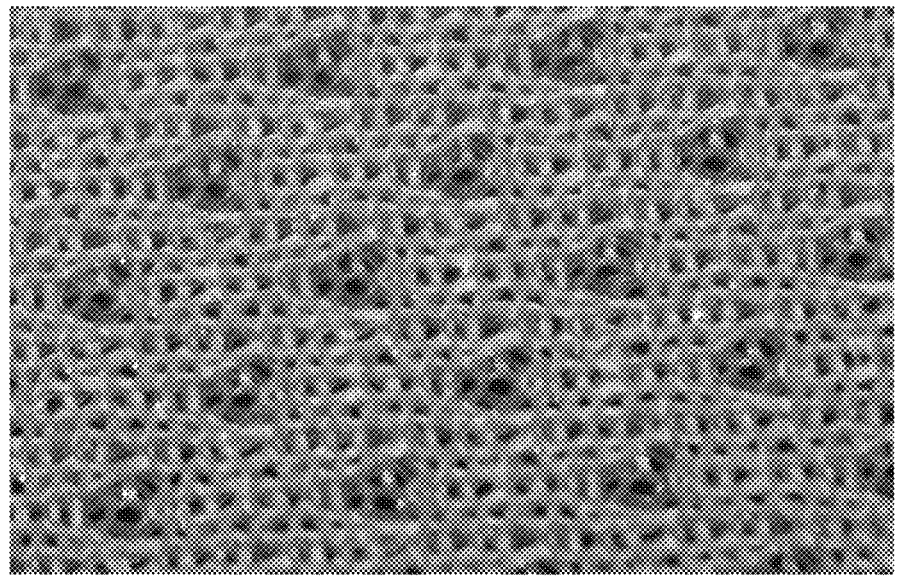
FIGS. 8A and 8B illustrate one embodiment of spacer layer material.
Figure 8B:
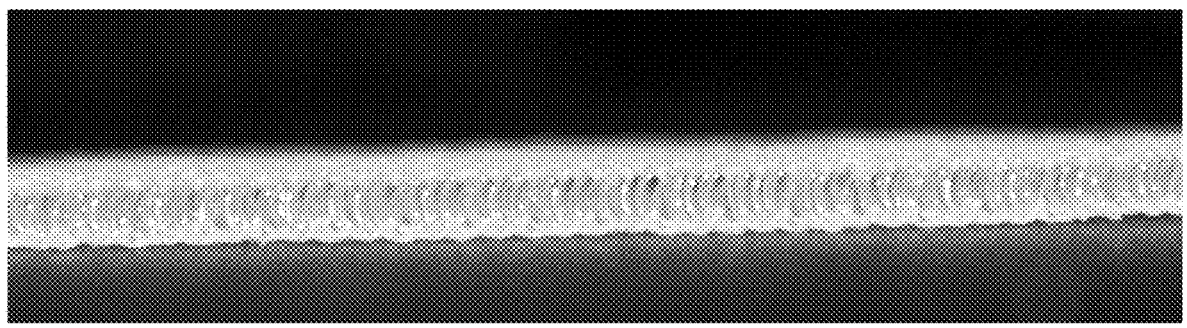

FIGS. 8A and 8B illustrate one embodiment of spacer layer material suitable for use as a transmission layer, which may be used in any of the dressing embodiments described above. The spacer or transmission material is preferably formed of a material having a three dimensional structure, and may have a top layer and a bottom layer comprising a knit pattern. For example, a knitted or woven spacer fabric (for example Baltex 7970 weft knitted polyester) or a non-woven fabric could be used. The top and bottom fabric layers may comprise polyester, such as 84/144 textured polyester or a flat denier polyester. Other materials and other linear mass densities of fiber could of course be used. In some embodiments, the top and bottom fabric layers may be the same pattern and the same material, and in other embodiments they may be different patterns and/or different materials. The top fabric layer may have more filaments in a yarn used to form it than the number of filaments making up the yarn used to form the bottom fabric layer, in order to control moisture flow across the transmission layer. Particularly, by having a filament count greater in the top layer, that is to say, the top layer is made from a yarn having more filaments than the yarn used in the bottom layer, liquid tends to be wicked along the top layer more than the bottom layer. FIG. 8A illustrates one possible knit pattern for a top or bottom fabric layer.

As illustrated in the side view of FIG. 8B, between the top and bottom fabric layers may be a plurality of filaments. The filaments may comprise a monofilament fiber or a multistrand fiber, and may be knitted polyester viscose or cellulose. In some embodiments, a majority of the filaments, by volume, may extend vertically (that is, perpendicular to the plane of the top and bottom layers), or substantially or generally vertically. In another embodiment, 80%-90% (or approximately 80% to approximately 90%) of the filaments or more, by volume, may extend vertically, or substantially or generally vertically. In another embodiment, all or substantially all of the filaments, by volume, may extend vertically, or substantially or generally vertically. In some embodiments, a majority, 80%-90% (or approximately 80% to approximately 90%) of the filaments or more, or even all or substantially all of the filaments, extend upward from the bottom fabric layer and/or downward from the top fabric layer, and in some embodiments, such filaments extend over a length more than half the distance between the top and bottom fabric layers. In some embodiments, a majority, 80%-90% (or approximately 80% to approximately 90%) of the filaments or more, or even all or substantially all of the filaments, span a distance that is greater in a direction perpendicular to the top and bottom fabric layers (a vertical direction) than in a direction parallel to the top and bottom fabric layers (a horizontal direction). The orientation of such filaments may promote vertical wicking of fluid through the spacer layer. In some embodiments, the ratio of the amount of fluid wicked vertically through the spacer material to the amount of fluid wicked laterally across the spacer material when under negative pressure may be 2:1 or more, or approximately 2:1 or more, or may be up to 10:1 or more, or approximately 10:1 or more, in some embodiments. Such filaments may also keep the top and bottom layers spaced apart when exposed to compressive forces or negative pressure.

Figure 9A:
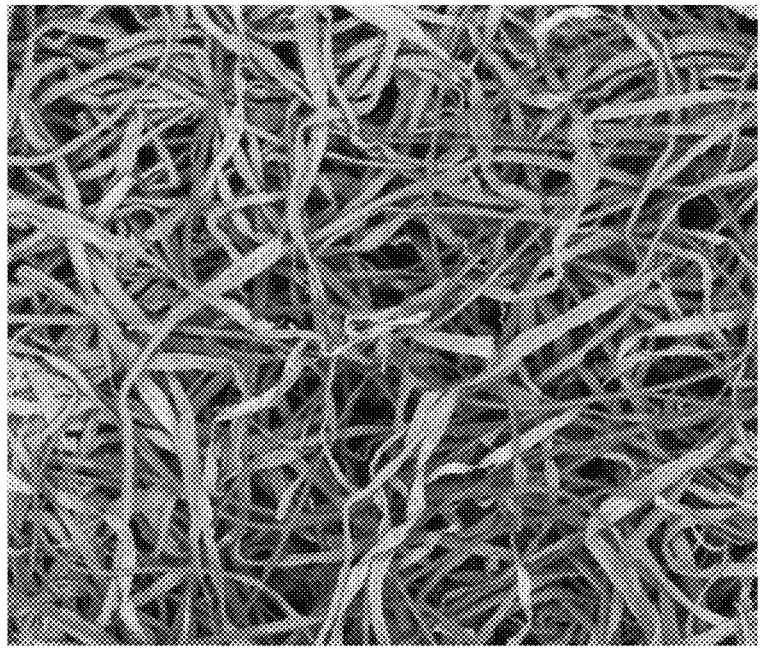
FIGS. 9A and 9B illustrate one embodiment of acquisition distribution layer material.
Figure 9B:
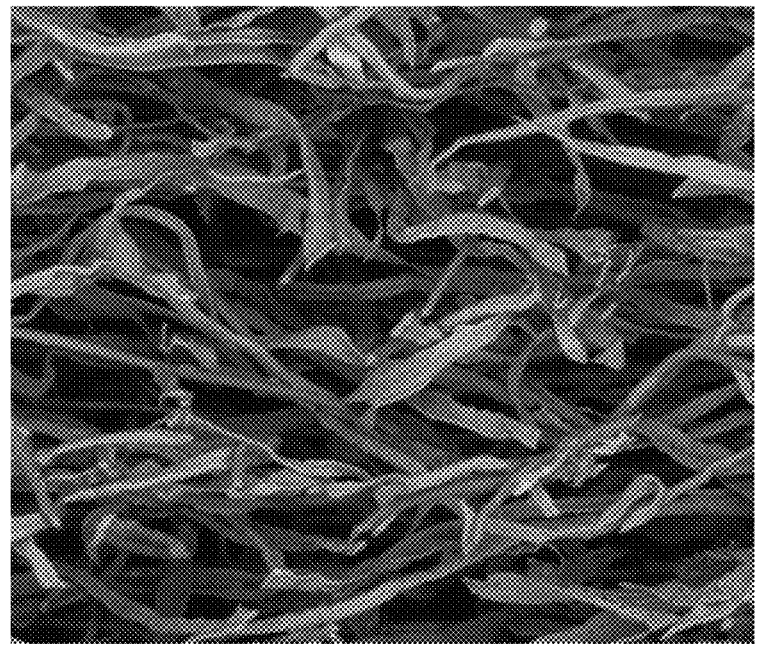

FIGS. 9A and 9B illustrate one embodiment of acquisition distribution layer material which may be suitable for use as a transmission layer in any of the dressing embodiments described above. To those versed in the art of acquisition distribution layers it would be obvious that other ADL materials may be used to achieve a similar effect. Such ADL layers may be composed of multiple fibre types and be complex in structure and design. The ADL material, in an uncompressed state, may be 0.1 mm to 4 mm thick, or approximately 0.1 mm to approximately 4 mm thick, and in some embodiments may be 1.2 mm thick, or approximately 1.2 mm thick, in an uncompressed state. The ADL material may comprise a plurality of loosely packed fibers, which may be arranged in a substantially horizontal fibrous network.

In some embodiments, the ADL material may consist of a mix of two fiber types. One may be a flat fiber which may be 20 µm to 50 µm in width, or approximately 20 µm to approximately 50 µm in width, and may comprise a cellulosic based material. The other fiber may be a two component fiber that has an inner core that is 8 µm to 10 µm in diameter, or approximately is 8 µm to approximately 10 µm in diameter, and an outer layer with a thickness of 1 µm to 2 µm, or approximately 1 µm to approximately 2µm. The two component fiber may be a mix of a polyethylene (PE) type material, and polyethylene terephthalate (PET). In some embodiments the inner core of the two component fiber may be PET and the outer layer may be PE. The PE/PET fibers may have a smooth surface morphology, while the cellulosic fibers may have a relatively rougher surface morphology. In some embodiments the ADL material may comprise about 60% to about 90% cellulosic fibers, for example approximately 75% cellulosic fibers, and may comprise about 10% to about 40% PE/PET fibers, for example approximately 25% PE/PET fibers.

FIG. 9A illustrates a backscatter scanning electron microscope (SEM) plan view of a sample portion of acquisition distribution layer material at 140× magnification. FIG. 9B illustrates an SEM cross sectional view at 250× magnification. As illustrated in FIG. 9B, a majority of the fiber volume may extend horizontally (that is, parallel to the plane of the top and bottom surfaces of the material), or substantially or generally horizontally. In another embodiment, 80%-90% (or approximately 80% to approximately 90%) or more of the fiber volume may extend horizontally, or substantially or generally horizontally. In another embodiment, all or substantially all of the fiber volume may extend horizontally, or substantially or generally horizontally. In some embodiments, a majority, 80%-90% (or approximately 80% to approximately 90%) of the fibers or more, or even all or substantially all of the fibers, span a distance perpendicular to the thickness of the ADL material (a horizontal or lateral distance) that is greater than the thickness of the ADL material. In some embodiments, the horizontal or lateral distance spanned by such fibers is 2 times (or about 2 times) or more, 3 times (or about 3 times) or more, 4 times (or about 4 times) or more, 5 times (or about 5 times) or more, or 10 times (or about 10 times) or more the thickness of the ADL material. The orientation of such fibers may promote lateral wicking of fluid through the ADL material. This may more evenly distribute fluid such as wound exudate throughout the ADL material. In some embodiments, the ratio of the amount of fluid wicked laterally across the ADL material to the amount of fluid wicked vertically through the ADL material under negative pressure may be 2:1 or more, or approximately 2:1 or more, or may be up to 10:1 or more, or approximately 10:1 or more, in some embodiments.

Figure 10A:
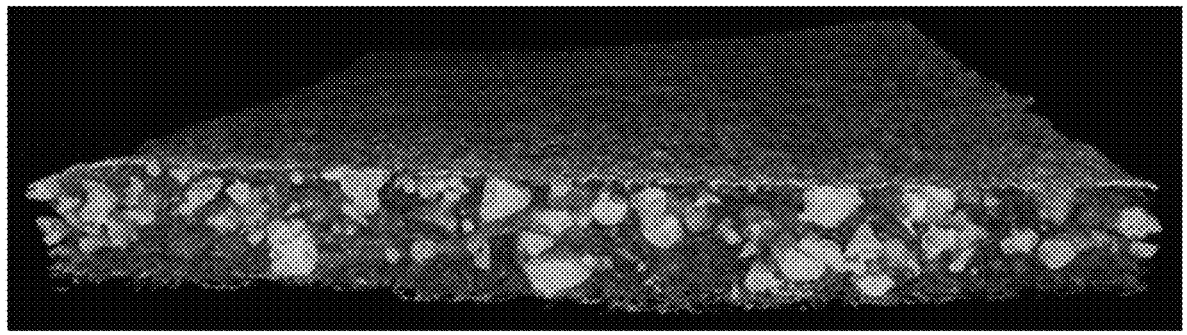
FIGS. 10A and 10B illustrate one embodiment of absorbent layer material.
Figure 10B:
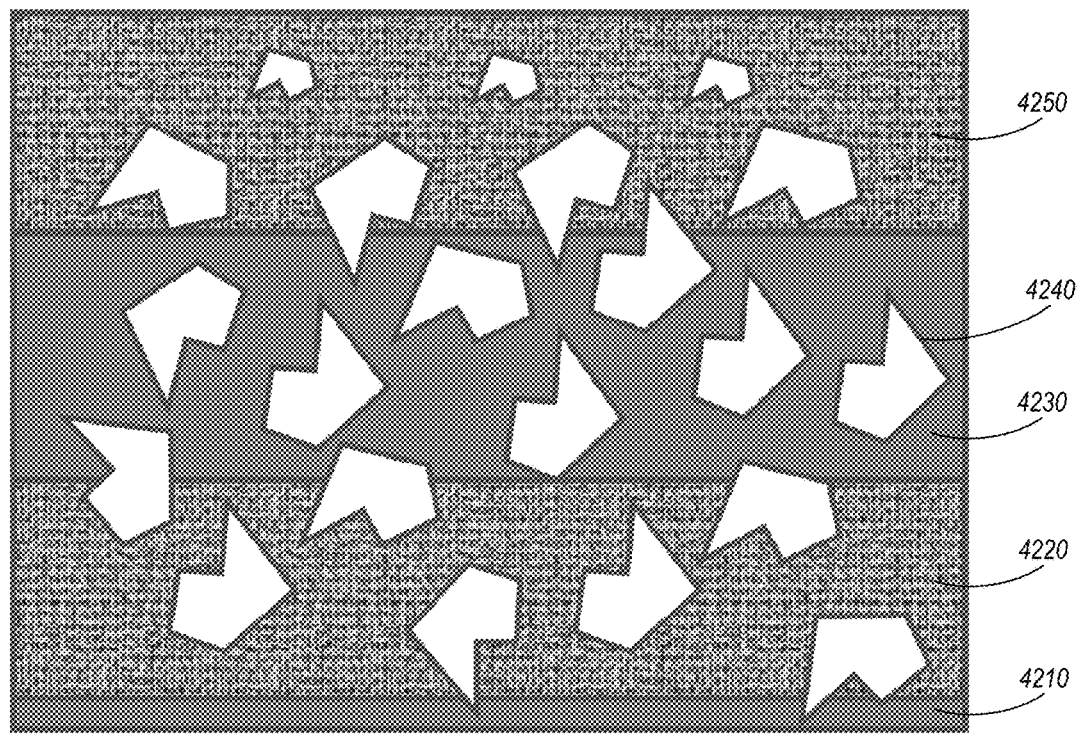

FIGS. 10A and 10B illustrate one embodiment of absorbent layer material which may be used in any of the dressing embodiments described above. FIG. 10A illustrates a three dimensional microtomographic cross sectional view of a sample of absorbent material, depicting a fibrous composition interspersed with superabsorbent particles.

FIG. 10B is a cross sectional schematic diagram of an embodiment of the absorbent material illustrating a plurality of layers within the absorbent material. The absorbent material may have a textured layer 4210 on one side of a fibrous network, the fibrous network defining the bulk of the absorbent material and comprising layers 4220, 4240, and

4250. Superabsorbent particles 4230 may be dispersed throughout layers 4220, 4240, and 4250. The textured layer 4210, also referred to as the "tissue dispersant layer" in above portions of this specification, may be configured to laterally transmit fluid. Though depicted as the lowermost layer of the absorbent material, the textured layer 4210 may in some embodiments be positioned as the uppermost layer of the absorbent material, and in some embodiments may be positioned as both the lowermost and uppermost layers of the absorbent material. The textured layer 4210 may comprise flat fibers 20 µm to 50 µm in width, or approximately 20 µm to approximately 50 µm in width. The textured layer 4210 may comprise 1 to 2 or approximately 1 to approximately 2 layers of the flat fibers, and the textured layer 4210 may have an overall thickness of 0.04 mm, or approximately 0.04 mm.

The bulk of the absorbent material, comprising layers 4220, 4240, and 4250, may have a thickness of 1.7 mm, or approximately 1.7 mm, or may have a thickness in the range of 0.5 mm to 5.0 mm, or about 0.5 mm to about 5.0 mm. The bulk of the absorbent material may comprise a mix of two fiber types arranged in a fibrous network, for example the cellulosic fiber having a width of 20 µm to 50 µm, or approximately 20 µm to approximately 50 µm, and the PE/PET composite fiber, described above with respect to the ADL material. The superabsorbent particles 4230 may be irregularly shaped and varied in size, and may have a diameter of up to 1 mm, or approximately 1 mm. The superabsorbent particles 4230 may comprise a sodium acrylate type material. There may be relatively fewer superabsorbent particles in a portion of the uppermost surface of the bulk of the absorbent material (the surface of layer 4250 opposite the textured layer 4210), for example in an uppermost surface having a thickness of approximately 0.1 mm.

Layer 4220 may be a liquid absorption layer configured to draw liquid upward through the material towards layers 4240 and 4250. Layer 4240 may be a storage layer configured to hold absorbed liquid. Layer 4220 may be a liquid distribution layer configured to apply a "reverse suction" effect to the liquid storage layer 4240 in order to inhibit (or substantially inhibit) absorbed liquid from leaking back down through the lower layers of the absorbent material, a phenomenon which is commonly known as "back wetting."

Superabsorbent particles 4230 may be distributed primarily within the storage layer, may extend partially into the absorption layer 4220 and liquid distribution layer 4250, or may be distributed evenly (or substantially evenly) throughout the layers. The layers 4220, 4240, and 4250 may overlap with a portion of adjacent layers, and may or may not be separable.

FIG. 11 illustrates one embodiment of an adhesive spread on approximately one square centimeter of a film material, which may be used as the cover or backing layer in any of the dressing embodiments described above. The adhesive on the film has been covered with carbon powder for ease of illustrating the spread of the adhesive. The adhesive may comprise, for example, an acrylate type adhesive, for example K5 adhesive, and may be laid down in a criss cross pattern. In some embodiments, the adhesive material may cover approximately 45.5%±approximately 1.3% of the film surface. The pattern and coverage of the adhesive may vary so long as the configuration is suitable for desired vapor permeability.

IV. Example Dressings with Plug Material

FIGS. 12A-12E are photographic representations of various embodiments of a wound dressing configured for enhanced tissue visibility through plug material. As described above, the plug material can be any soft, transparent or translucent, and optionally hydrophobic material, with one example being silicone. Plug material can be positioned within some or all through holes in the dressing.

Figure 12A:
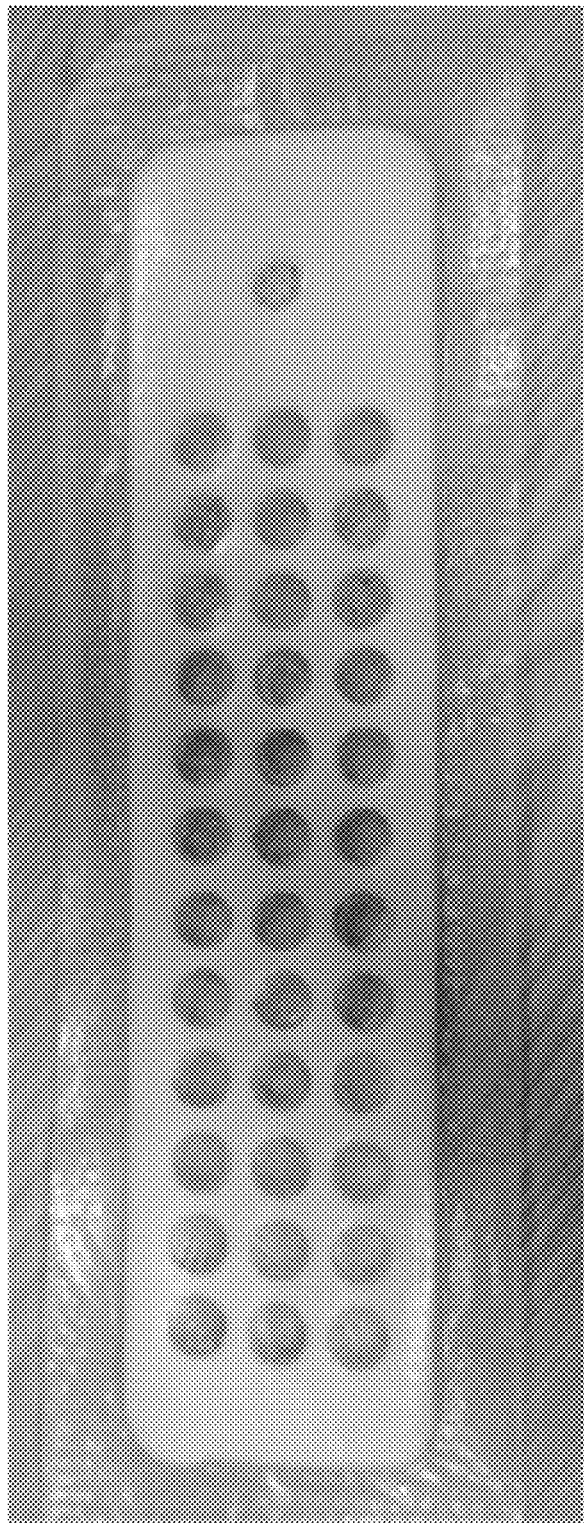
FIGS. 12A-12E are photographic representations of various embodiments of a wound dressing configured for enhanced tissue visibility through plug material.

FIG. 12A illustrates one embodiment of a wound dressing having at least one internal layer positioned between a cover layer and a wound contact layer having a sealed perimeter, the at least one internal layer having a first through hole positioned so as to underlie a suction port (not attached in this illustration) and a viewing window matrix of additional through holes windows through the dressing. In this embodiment, each hole in the viewing window matrix is provided with a pillar of plug material. The through hole to underlie the suction port may not be provided with plug material. In certain embodiments, the at least one internal layer includes two or more layers (e.g., a transmission layer and an absorbent layer over the transmission layer), and the pillar of plug material can extend fully through both of the layers. In some embodiments, the through holes of the transmission layer and the absorbent layer may have the same dimension or diameter. In other implementations, the pillar of plug material can extend through just one layer, or at least partially through one or more layers. The pillars of plug material can have a diameter of 10 mm (or approximately 10 mm) in some examples.

Figure 12B:
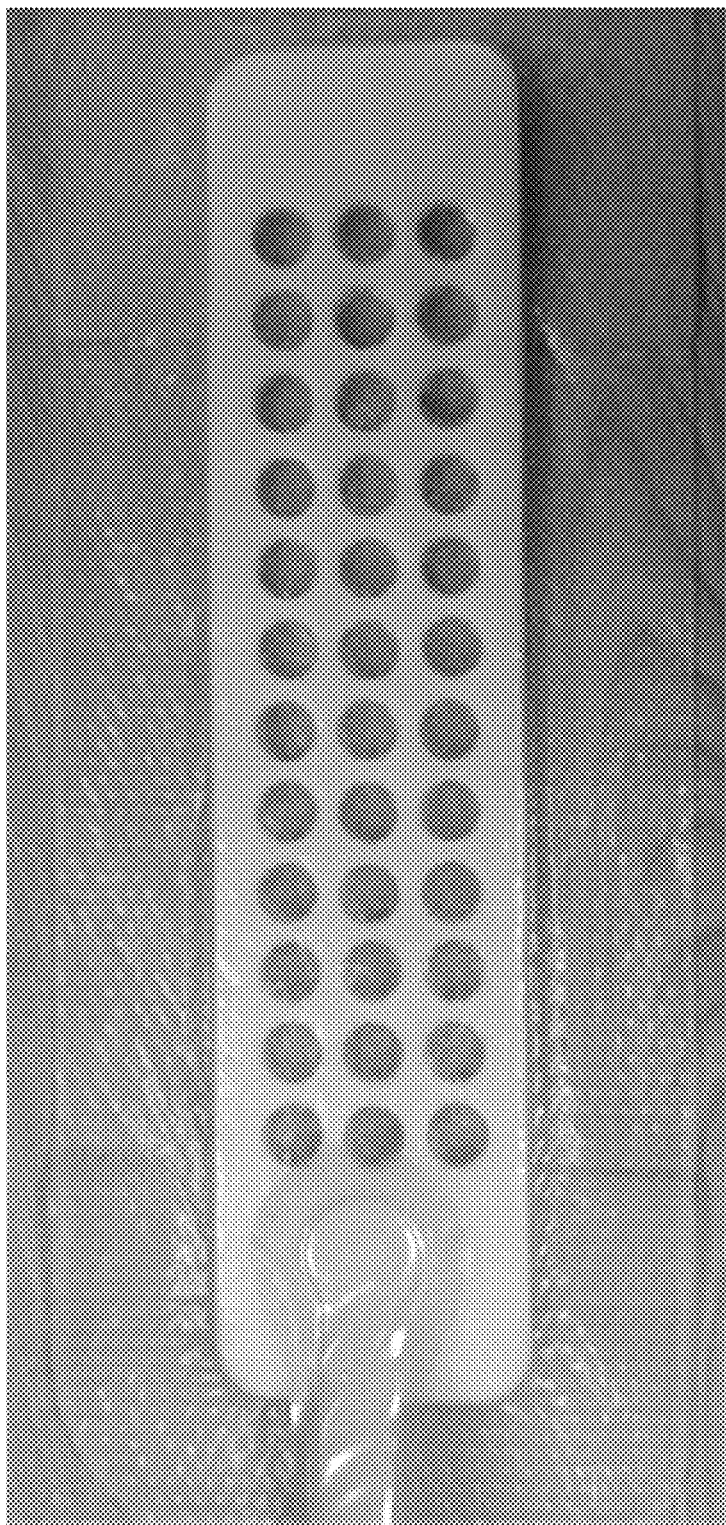
Figure 12C:

FIG. 12B illustrates another embodiment of a wound dressing having at least one internal layer with a viewing window matrix having the through holes filled with pillars of plug material. The embodiment of FIG. 12B includes a flexible suction adapter attached to the cover layer of the dressing over the first through hole. FIG. 12C illustrates the embodiment of FIG. 12B with the suction adapter attached to a portable, compact negative pressure pump. In other embodiments a length of extension tubing may be coupled between the pump and the suction adapter, and various other negative pressure pumps may be coupled to the system in place of the illustrated compact pump.

Figure 12D:

FIG. 12D illustrates a close-up view of a portion of the viewing window matrix of the embodiment of FIG. 12B, each through hole in the viewing matrix having a pillar of plug material extending through both an absorbent layer and a transmission layer positioned underneath the absorbent layer. The through holes forming the viewing windows can be aligned and can have a diameter of 10 mm (or approximately 10 mm), and the pillars of plug material can have a diameter of 10 mm (or approximately 10 mm) in some examples.

Figure 12E:
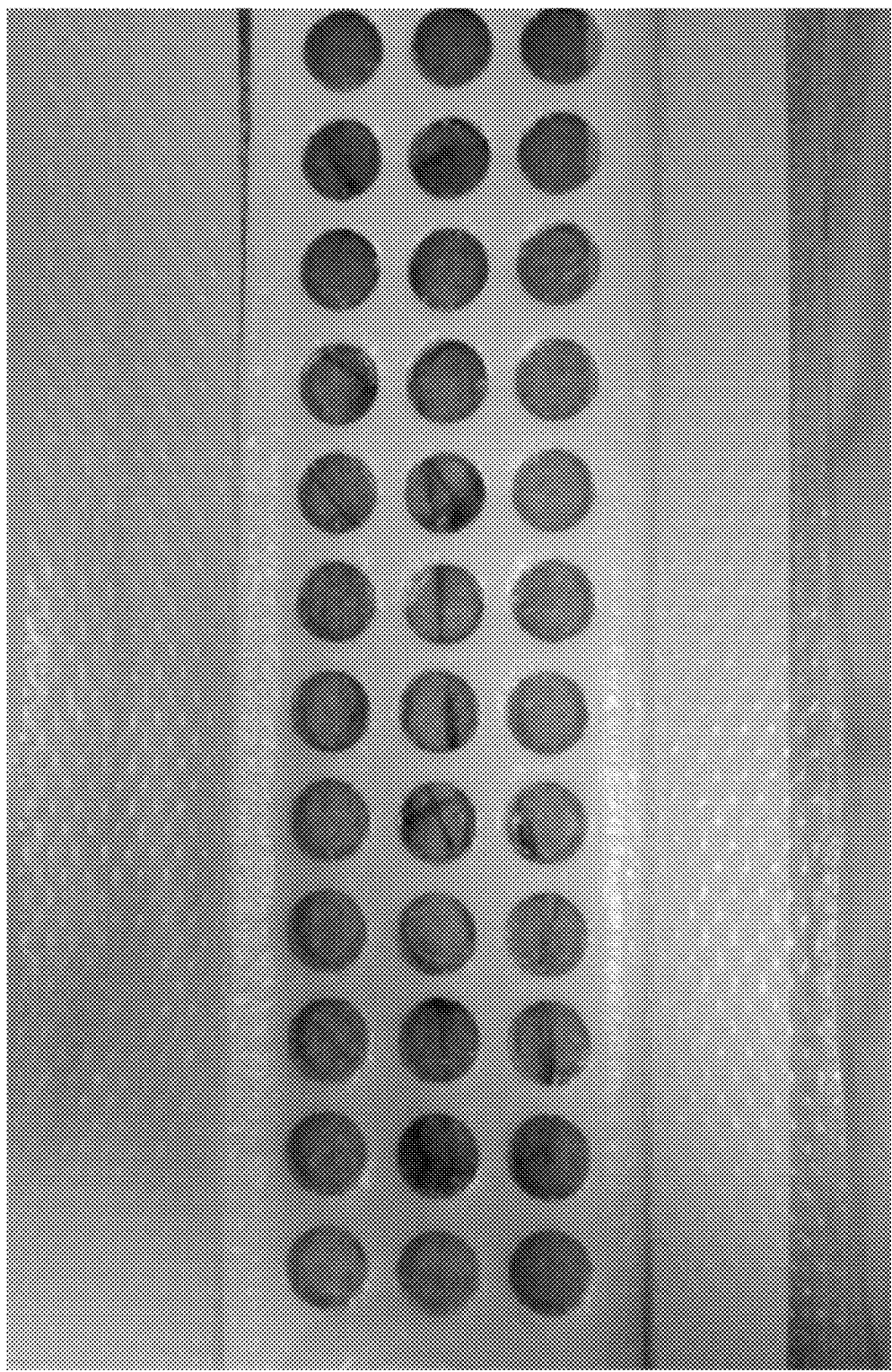

FIG. 12E illustrates a visual example of the enhanced visibility provided by a dressing with viewing windows such as is described herein. The illustrated dressing is placed over a surface with a variety of markings that are clearly visible through the viewing windows. Accordingly, a clinician can use such a dressing to visually assess the condition of tissue underlying the dressing.

In an alternate embodiment, a dressing can include a transmission layer that is transparent, translucent, or contains more open areas (e.g., a less dense weave) with holes smaller than approximately 10 mm in diameter, and the pillars may only extend through the absorbent layer. Accordingly, the transmission layer may extend underneath the pillars of plug material in the absorbent layer, thereby providing enhanced transmission of negative pressure and/or spread of wound exudate compared to embodiments having plug material positioned within the transmission layer.

In another alternate embodiment, rather than having the plug material formed as pillars through one or more layers, a dressing may have a layer or structure of transparent or translucent material (for example, silicone) with an array of absorbent or superabsorbent material portions. For instance, the transparent or translucent layer or structure may form an interconnected frame extending across the length and width of the wound dressing, and have a matrix of holes or spaces within the frame where absorbent material can be provided to fill the holes or spaces. In some examples, the transparent or translucent layer may take the same shape as any of the embodiments of the absorbent layer previously described, and the superabsorbent material portions may take the shape of any of the embodiments of the pillars previously described. Alternatively, a dressing may comprise alternating struts, strips or bands of transparent or translucent material and struts, strips or bands of absorbent material. For example, a wound dressing layer may comprise diagonal alternating bands of transparent or translucent material and absorbent material. In any of the aforementioned embodiments, a transmission layer may be provided under the transparent or translucent material and the absorbent material for transmission of negative pressure, and a suction adapter or other negative pressure source may be provided to communicate negative pressure to a wound site, optionally through a through hole in either the absorbent material or in the transparent or translucent material.

V. Terminology

Features, materials, characteristics, or groups described in conjunction with a particular aspect, embodiment, or example are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

While certain embodiments have been described, these embodiments have been presented by way of example only, and are not intended to limit the scope of protection. Indeed, the novel methods and systems described herein may be embodied in a variety of other forms. Furthermore, various omissions, substitutions and changes in the form of the methods and systems described herein may be made. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure.

Although the present disclosure includes certain embodiments, examples and applications, it will be understood by those skilled in the art that the present disclosure extends beyond the specifically disclosed embodiments to other alternative embodiments and/or uses and obvious modifications and equivalents thereof, including embodiments which do not provide all of the features and advantages set forth herein. Accordingly, the scope of the present disclosure is not intended to be limited by the specific disclosures of preferred embodiments herein, and may be defined by claims as presented herein or as presented in the future.

What is claimed is:

1. A wound dressing comprising:
   a material layer;
   a plurality of plug materials extending vertically through a thickness of the material layer; and
   a cover layer positioned above the material layer, the cover layer configured to form a negative pressure chamber underneath the cover layer, the cover layer couplable to a source of negative pressure configured to create negative pressure in the negative pressure chamber.

2. The wound dressing of claim 1, further comprising a port configured to communicate negative pressure to the negative pressure chamber.

3. The wound dressing of claim 2, wherein the port is configured to be attached to the cover layer.

4. The wound dressing of claim 1, wherein the material layer comprises a foam.

5. The wound dressing of claim 1, wherein the cover layer is transparent or translucent.

6. The wound dressing of claim 1, wherein the material layer comprises a plurality of through holes extending vertically through the thickness of the material layer, wherein the plug materials are positioned within at least some of the plurality of through holes.

7. The wound dressing of claim 6, wherein the through holes are configured to permit viewing of tissue beneath the wound dressing through the cover layer when the wound dressing is applied to a patient.

8. The wound dressing of claim 1, wherein the plug materials are cylindrical.

9. A method of treating a wound, the method comprising:
   applying a wound dressing to the wound, the wound dressing comprising:
      a material layer;
      a plurality of plug materials extending vertically through a thickness of the material layer; and
      a cover layer positioned above the material layer, the cover layer configured to form a negative pressure chamber underneath the cover layer, the cover layer couplable to a source of negative pressure configured to create negative pressure in the negative pressure chamber.

10. The method of claim 9, wherein the wound dressing further comprises a port configured to communicate negative pressure to the negative pressure chamber.

11. The method of claim 10, wherein the port is configured to be attached to the cover layer.

12. The method of claim 9, wherein the material layer comprises a foam.

13. The method of claim 9, wherein the cover layer is transparent or translucent.

14. The method of claim 9, wherein the material layer comprises a plurality of through holes extending vertically through the thickness of the material layer, wherein the plug materials are positioned within at least some of the plurality of through holes.

15. The method of claim 14, further comprising visualizing tissue beneath the wound dressing through the cover layer through the through holes.

16. The method of claim 9, wherein the plug materials are cylindrical.

17. A dressing, comprising:
   a foam layer;

a plurality of cores extending substantially through the foam layer; and a drape sealable over the foam layer and a wound bed, the drape defining a substantially-airtight volume between the drape and the wound bed that contains the foam layer, the drape couplable to a pump operable to create a negative pressure in the substantially-airtight volume.

\* \* \* \* \*

UNITED STATES PATENT AND TRADEMARK OFFICE
CERTIFICATE OF CORRECTION

| | |
|---|---|
| PATENT NO. | : 11,596,552 B2 |
| APPLICATION NO. | : 16/841516 |
| DATED | : March 7, 2023 |
| INVENTOR(S) | : Edward Yerbury Hartwell |

It is certified that error appears in the above-identified patent and that said Letters Patent is hereby corrected as shown below:

On the Title Page

On Page 6, Column 2, Line 20, under Other Publications, delete "(4"x4')," and insert --(4"x4"),--.

In the Specification

In Column 2, Line 55, delete "thicknesss" and insert --thickness--.

In Column 3, Line 23, delete "diamond-shaped. T" and insert --diamond-shaped.--.

In Column 4, Line 50, delete "sterniotomies," and insert --sternotomies,--.

In Column 16, Lines 2-3, delete "Versapore™" and insert --Versapor™--.

In Column 16, Line 30, delete "preformed" and insert --performed--.

In Column 20, Lines 7-23, delete "µm to approximately 50 µm in width, and may comprise a cellulosic based material. The other fiber may be a two component fiber that has an inner core that is 8 µm to 10 µm in diameter, or approximately is 8 µm to approximately 10 µm in diameter, and an outer layer with a thickness of 1 µm to 2 µm, or approximately 1 µm to approximately 2µm. The two component fiber may be a mix of a polyethylene (PE) type material, and polyethylene terephthalate (PET). In some embodiments the inner core of the two component fiber may be PET and the outer layer may be PE. The PE/PET fibers may have a smooth surface morphology, while the cellulosic fibers may have a relatively rougher surface morphology. In some embodiments the ADL material may comprise about 60% to about 90% cellulosic fibers, for example approximately 75% cellulosic fibers, and may comprise about 10% to about 40% PE/PET fibers, for example approximately 25% PE/PET fibers." and insert the same on Column 20, Line 6, as a continuation of the same paragraph.

In Column 21, Line 60, delete "±approximately" and insert --± approximately--.

Signed and Sealed this
Thirteenth Day of June, 2023

Katherine Kelly Vidal
*Director of the United States Patent and Trademark Office*